(12) United States Patent
Charvet

(10) Patent No.: US 11,576,952 B2
(45) Date of Patent: Feb. 14, 2023

(54) INJECTABLE SOLUTION AT PH 7 COMPRISING AT LEAST ONE BASAL INSULIN FOR WHICH THE PI IS FROM 5.8 TO 8.5 AND A CO-POLYAMINO ACID BEARING CARBOXYLATE CHARGES AND HYDROPHOBIC RADICALS

(71) Applicant: ADOCIA, Lyons (FR)

(72) Inventor: Richard Charvet, Rillieux la Pape (FR)

(73) Assignee: ADOCIA, Lyons (FR)

( * ) Notice: Subject to any disclaimer, the term of this patent is extended or adjusted under 35 U.S.C. 154(b) by 0 days.

(21) Appl. No.: 16/641,383

(22) PCT Filed: Aug. 24, 2018

(86) PCT No.: PCT/EP2018/072936
§ 371 (c)(1),
(2) Date: Sep. 11, 2020

(87) PCT Pub. No.: WO2019/038445
PCT Pub. Date: Feb. 28, 2019

(65) Prior Publication Data
US 2020/0405819 A1 Dec. 31, 2020

(30) Foreign Application Priority Data
Aug. 24, 2017 (FR) ...................... 1757860

(51) Int. Cl.
*A61K 38/00* (2006.01)
*A61K 38/28* (2006.01)
*A61K 9/00* (2006.01)
*A61K 38/26* (2006.01)
*A61K 47/42* (2017.01)

(52) U.S. Cl.
CPC ............ *A61K 38/28* (2013.01); *A61K 9/0019* (2013.01); *A61K 38/26* (2013.01); *A61K 47/42* (2013.01)

(58) Field of Classification Search
CPC ...... A61K 9/0019; A61K 38/28; A61K 47/34; A61K 47/36; A61K 9/08; A61K 47/12; A61K 47/02; A61K 47/26; A61K 2300/00; A61K 31/721; A61K 31/715; A61K 38/26; A61K 47/183; A61K 47/61; A61K 9/19; A61K 31/00; A61K 45/06; A61K 47/10; A61K 47/42; A61K 31/12; A61K 31/13; A61K 31/33; A61K 31/335; A61K 31/69; A61K 31/70; A61K 33/06; A61K 33/42; A61K 38/00; A61K 38/02; A61K 38/22; A61K 47/06; A61K 47/22; A61K 47/28; A61K 47/32; A61K 47/56; A61K 47/30; A61K 47/6455; A61K 9/2045; A61K 9/5084; C08B 37/0021; C08B 37/0018; C08B 37/0045; C08B 37/0072; C08B 37/0084; C08B 37/0006; C08B 37/0024; C08B 37/0054; C08B 37/0057; C08B 37/00; C08B 1/00; C08B 37/0009; C08B 37/006; A61P 3/10; A61P 19/00; A61P 43/00; A61P 3/08; A61P 17/02; A61P 5/48; C07H 15/18; C07H 3/06; C07H 15/04; C07H 15/26; C07K 5/00; C07K 2319/30; C07K 5/06086; C07K 14/62; C07K 2/00; C08G 69/10; C08G 18/6484; C08G 18/711; C08L 5/02; C08L 5/00; C08L 5/04; C08L 5/08; C07C 235/74; C07C 271/22; C07C 233/00; C07D 207/16; C07D 311/72; C07D 403/12; C07D 403/14; C07J 41/0055; Y02E 10/542; Y02E 10/549
See application file for complete search history.

(56) References Cited

U.S. PATENT DOCUMENTS

| | | | |
|---|---|---|---|
| 5,656,722 A | 8/1997 | Dorschug | |
| 6,100,376 A | 8/2000 | Dorschug | |
| 2010/0233084 A1* | 9/2010 | Narasimhaswamy | ...................... A61K 47/6911 424/9.1 |
| 2017/0348423 A1* | 12/2017 | Geissler | ................. A61K 47/56 |

FOREIGN PATENT DOCUMENTS

| | | |
|---|---|---|
| FR | 2801226 A1 | 5/2001 |
| FR | 2840614 A1 | 12/2003 |
| WO | 2004/096854 A2 | 11/2004 |

(Continued)

OTHER PUBLICATIONS

Hua Lu et al.; "N-Trimethylsilyl Amines for Controlled Ring-Opening Polymerization of Amino Acid N-Carboxyanhydrides and Facile End Group Functionalization of Polypeptides;" J. Am. Chem. Soc.; Sep. 3, 2008; pp. 12562-S8.

(Continued)

*Primary Examiner* — Aradhana Sasan
*Assistant Examiner* — Mercy H Sabila
(74) *Attorney, Agent, or Firm* — Oliff PLC

(57) ABSTRACT

A composition in the form of an injectable aqueous solution, whose pH consists from 6.0 to 8.0, including at least: a basal insulin whose isoelectric point includes from 5.8 to 8.5; a co-polyamino-acid bearing carboxylate charges and hydrophobic radicals Hy, the co-polyamino-acid being constituted of glutamic or aspartic units and said hydrophobic radicals Hy according to the following formula I:

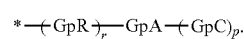

Formula I

18 Claims, 1 Drawing Sheet

(56) References Cited

FOREIGN PATENT DOCUMENTS

| WO | 2010/063124 A1 | 6/2010 |
| WO | 2013/021143 A1 | 2/2013 |
| WO | 2013/104861 A1 | 7/2013 |
| WO | 2014/124993 A1 | 8/2014 |
| WO | 2014/124994 A1 | 8/2014 |
| WO | 2003/053339 A2 | 11/2014 |

OTHER PUBLICATIONS

Hua Lu et al.; "Hexamethyldisilazane-Mediated Controlled Polymerization of a-Amino Acid N-Carboxyanhydrides" J Am. Chern. Soc.; Oct. 27, 2007; p. 14114-14115.

Timothy J. Deming; "Facile Synthesis of Block Copolypeptides of Defined Architecture;" Nature; Nov. 27, 1997; vol. 390; pp. 386-389.

Timothy J. Deming; "Polypeptide and Polypeptide Hybrid Copolymer Synthesis via NCA Polymerization;" Adv Polym Sci; Feb. 23, 2006; pp. 1-18.

* cited by examiner

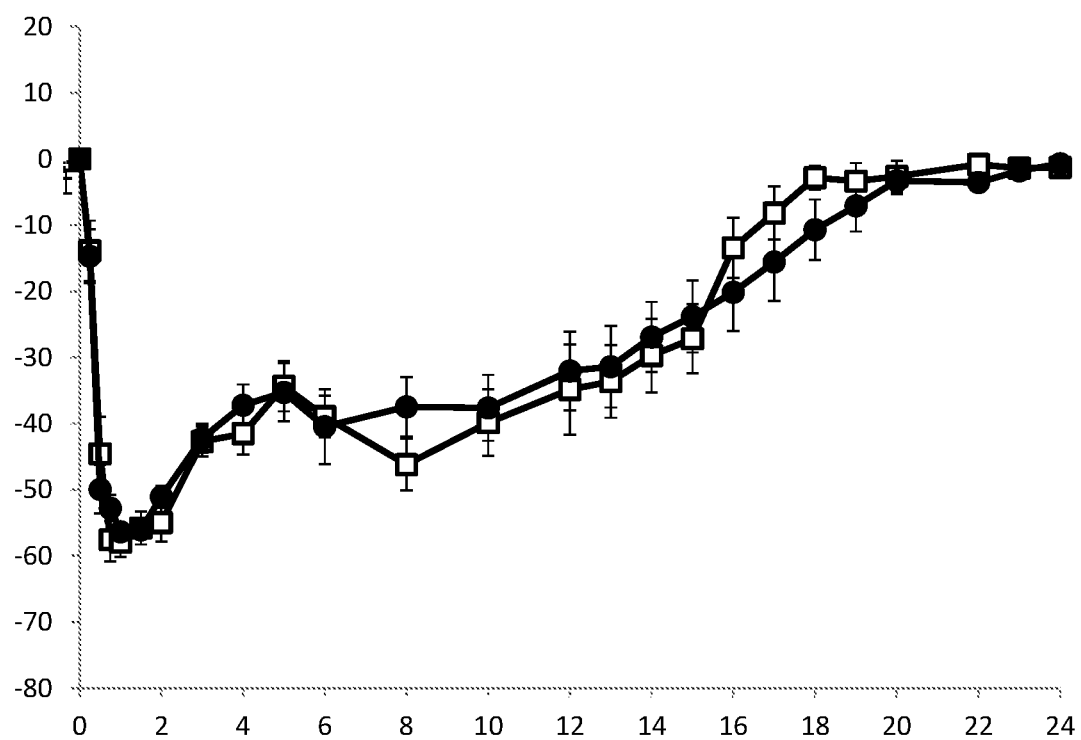

INJECTABLE SOLUTION AT PH 7 COMPRISING AT LEAST ONE BASAL INSULIN FOR WHICH THE PI IS FROM 5.8 TO 8.5 AND A CO-POLYAMINO ACID BEARING CARBOXYLATE CHARGES AND HYDROPHOBIC RADICALS

This is a National Phase of International Application No. PCT/EP2018/072936 filed Aug. 24, 2018, which claims the benefit of French Application No. 1757860 filed Aug. 24, 2017.

The invention concerns insulin injection therapies for treating diabetes.

The invention relates to physically stable compositions in the form of an injectable aqueous solution, the pH of which is comprised from 6.0 to 8.0, comprising at least one basal insulin whose isoelectric point (pI) is comprised from 5.8 to 8.5, and a co-polyamino acid bearing carboxylate charges and hydrophobic radicals.

Insulin therapy, or diabetes treatment by insulin injection, has in recent years seen remarkable progress, specifically due to the development of new insulins, with a better blood sugar correction in patients in comparison with human insulin, and which have made possible improved simulation of the physiological activity of the pancreas.

When type II diabetes is diagnosed in a patient, treatment is implemented gradually. First, the patient takes oral anti-diabetics (OAD) such as Mandformin. When OADs alone are no longer sufficient to control the level of glucose in the blood, a change in treatment must be made and, depending on patient specificities, different treatment combinations can be implemented. For example, the patient may be treated with insulin glargine-type basal insulin or insulin det emir, in addition to OADs, then, depending on the evolution of the disease, with basal insulin and prandial insulin.

Furthermore, today, in order to make the transition from treatments by OADs, when the latter are no longer able to control the level of glucose in the blood, to a basal insulin/prandial insulin treatment, injection of GLP-1 RA analogues is recommended.

GLP-1 RA, for Glucagon-Like Peptide-1 receptor agonists, are insulinotropic peptides or incret ins, and belong to the family of gastro-intestinal hormones (or Gut Hormones) which stimulate the secretion of insulin when blood sugar is too high, for example, after a meal.

Gastro-intestinal hormones (Gut hormones) are also called satiety hormones. Specifically, they comprise GLP-1 RA (Glucagon like peptide-1 receptor agonist) and GIP (Glucose-dependent insulinotropic peptide), oxyntomodulin (a derivative of proglucagon), the peptide YY, amylin, cholecystokinin, pancreatic polypeptide (PP), ghrelin and enterostatin, which are peptidic or proteic structures. They also stimulate the secretion of insulin in response to glucose and fatty acids and are, therefore, as such, potential candidates for the treatment of diabetes.

Among these, the GLP-1 RA are those that have provided, to date, the best results in the development of drugs. They have made it possible for patients affected by type II diabetes to lose weight, while maintaining better control of their blood sugar.

Thus, GLP-1 RA analogues or derivatives have been developed, in particular to improve their stability.

On the other hand, in order to mean his daily insulin needs, a diabetic patient currently has available, schematically, two types of insulins with complementary actions: prandial insulins (or so-called rapid-acting insulins) and basal insulins (or so-called slow-acting insulins)

Prandial insulins allow rapid management (metabolization and/or storing) of the glucose provided during meals and snacks. The patient must inject himself with a prandial insulin before each food intake, or about 2 to 3 injections per day. The most widely used prandial insulins are: recombinant human insulin, NovoLog® (NOVO NORDISK insulin aspart), Humalog® (ELI LILLY insulin aspart) and Apidra® (SANOFI insulin glulisine).

Basal insulins ensure the maintenance of the patient's glycemic homeostasis outside the periods of food intake. Essentially, they act to block the production of endogenous glucose (hepatic glucose). The daily dose of basal insulin generally corresponds to 40-50% of the total daily insulin needs. Depending on the basal insulin used, this dose is dispensed in 1 or 2 injections, regularly distributed over the course of the day. The most commonly used basal insulins are Levemir® (NOVO NORDISK insulin detemir) and Lantus® (SANOFI insulin glargine).

In the interest of being thorough, it should be noted that NPH (insulin NPH for Neutral Protamine Hagedorn; Humiline NPH®, Insulatard®) is the oldest basal insulin. This formulation is derived from precipitating human insulin (anionic at neutral pH) by a cationic protein, protamine. The microcrystals formed in this process are dispersed in an aqueous suspension and dissolve slowly after subcutaneous injection. This slow dissolution ensures extended insulin release. However, this release does not ensure a constant concentration of insulin over time. The release profile is bell-shaped and lasts only from 12 to 16 hours. Therefore, it is injected twice a day. This NPH basal insulin is much less effective than the modern basal insulins, Levemir® and Lantus®. NPH is an intermediate-acting basal insulin.

The principle of NPH evolved with the appearance of rapid insulin analogues which include products called "Pre-mix" offering both rapid action and intermediate action. Novolog Mix® (NOVO NORDISK) and Humalog Mix® (ELI LILLY) are formulations comprising a rapid insulin analog, Novolog® and Humalog®, partially complexed with protamine. Thus, these formulations contain insulin analog microcrystals, whose action is called intermediary, and a part of the insulin that remained soluble whose action is rapid. These formulations do offer the advantage of a rapid acting insulin, but they also have the disadvantage of NPH, namely, a duration of action limited to from 12 to 16 hours, and insulin released in a "bell" curve. However, these products allow the patient to inject an intermediate action basal insulin with a rapid-action prandial insulin. However, numerous patients are concerned about reducing the number of their injections.

Basal insulins currently on the market may be classified according to the technical solution that allows to obtain extended action and, presently, two approaches are used.

The first, that of insulin detemir, is the binding to albumin in vivo. It is an analog, soluble at pH 7, which comprises a fatty acid side chain (tetradecanoyl) attached to position B29 which, in vivo, allows this insulin to associate with albumin. Its extended action is principally due to this affinity for albumin after subcutaneous injection.

However, its pharmacokinetic profile does not allow it to last an entire day, so that it is most frequently used in two injections per day.

Another insulin soluble at pH 7 is insulin degludec, marketed under the name Tresiba®. It also comprises a fatty acid side chain attached to the insulin (hexadecantioyl-γ-L-Glu).

The second, that of insulin glargine, is the precipitation at physiological pH. Insulin glargine is an analog of human insulin obtained by elongation of the C-terminal part of the B chain of human insulin by two arginine residues, and by substitution of the asparagine residue A21 with a glycine residue (U.S. Pat. No. 5,656,722). The addition of two arginine residues was designed to adjust the pI (isoelectric point) of insulin glargine to the physiological pH, and thus to make this analog to human insulin insoluble in the physiological medium.

In addition, the substitution of A21 was designed in order to make insulin glargine stable at acidic pH and to thus be able to formulate it in the form of an injectable solution at acidic pH. At the time of sub-cutaneous injection, the passage of insulin glargine from an acidic pH (pH 4-4.5) to a physiological pH (neutral pH) causes its precipitation under the skin. The slow redissolution of microparticle of insulin glargine ensures a slow and extended action.

The blood sugar lowering effect of insulin glargine is quasi-constant over a 24-hour period which allows most patients to only inject themselves once a day.

Insulin glargine is considered today as the most widely used basal insulin.

However, the necessarily acidic pH of basal insulin formulations, whose isoelectric point is comprised from 5.8 to 8.5, of insulin glargine type, may be a real problem, because this acidic pH of the insulin glargine formulation sometimes causes pain at injection in patients and, especially, prevents any formulation with other proteins, in particular, with prandial insulins, because the latter are not stable at acidic pH. The impossibility according to formulating a prandial insulin, at acidic pH, relates to the fact that prandial insulin undergoes, in these conditions, a secondary deamidation at position A21, which makes it impossible to mean the stability requirements applicable to injectable drugs.

At present, in applications WO 2013/021143 A1, WO 2013/104861 A1, WO 2014/124994 A1 and WO 2014/124993 A1, it was demonstrated that it was possible to solubilize these insulin glargine-type basal insulins, whose isoelectric point is comprised from 5.8 to 8.5, at neutral pH, while maintaining a difference in solubility between the in vitro medium (the container) and the in vivo medium (under the skin) regardless of the pH.

Application WO 2013/104861 A1 in particular describes compositions in the form of an injectable aqueous solution, whose pH is comprised from 6.0 to 8.0, comprising at least: a) one basal insulin whose isoelectric point (pI) is comprised from 5.8 to 8.5, and b) a copolyamino acid bearing carboxylate charges and hydrophobic radicals.

These compositions of the prior art have the major disadvantage of not being sufficiently stable to mean the specifications applicable to pharmaceutical formulations.

Therefore, there is a need to find a solution which allows to make a basal insulin soluble whose isoelectric point (pI) is comprised from 5.8 to 8.5, while preserving its basal profile after injection, but which also allows to satisfy the standard physical stability conditions for insulin-based pharmaceutical products.

Surprisingly, the applicant has found that the copolyamino acids that carry carboxylate charges and hydrophobic radicals according to the invention make it possible to obtain compositions in the form of solutions which, not only mean the requirements described in WO 2013/104861 A1, but which also are able to provide improved physical stability to said compositions without having to increase the number of excipients used.

These performances, a priori never reached, are also maintained when the basal insulin whose isoelectric point is comprised from 5.8 to 8.5, is associated in the composition with a prandial insulin and/or a gastrointestinal hormone.

Thus, surprisingly, the affinity of copolyamino acids according to the invention for insulin glargine was increased in that it allows to obtain the solubilization and stabilization of insulin glargine solutions at a ratio [Hy]/[basal insulin] lower than that of the prior art; in addition, these results are obtained without altering, and are even improving, the propensity of insulin glargine to precipitate, as demonstrated in the experimental part.

This improvement in the affinity also makes it possible, in the context of chronic treatments, to limit the level of exposure to said excipients.

The copolyamino acids bearing carboxylate charges and hydrophobic radicals Hy according to the invention have an excellent resistance to hydrolysis. This can be specifically verified under accelerated conditions, for example, at basic pH (pH 12) by hydrolysis tests.

In addition, forced oxidation tests, for example of the Fenton oxidation type, show that the copolyamino acids bearing carboxylate charges and hydrophobic radicals Hy have a good resistance to oxidation.

Thus, the invention concerns physically stable compositions in the form of an injectable aqueous solution, whose pH is comprised from 6.0 to 8.0, comprising at least:

a) a basal insulin whose isoelectric point (pI) is comprised from 5.8 to 8.5, b) A co-polyamino-acid bearing carboxylate charges and at least a hydrophobic radical according to the following formula I Thus, the invention concerns physically stable compositions in the form of an injectable aqueous solution, whose pH is comprised from 6.0 to 8.0, comprising at least:

a) a basal insulin whose isoelectric point (pI) is comprised from 5.8 to 8.5;

b) A co-polyamino-acid bearing carboxylate charges and hydrophobic radicals Hy, said co-polyamino-acid being constituted of glutamic or aspartic units and said hydrophobic radicals Hy according to the following formula I:

Formula I

Wherein

GpR is a radical according to formula II or II':

    II or

    II';

GpA is a radical according to formula III or III':

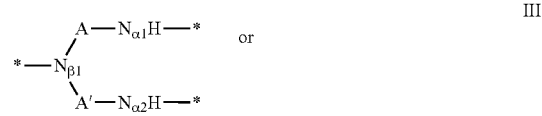    III

-continued

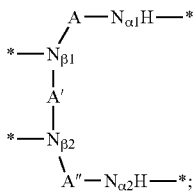

GpC is a radical according to formula IV:

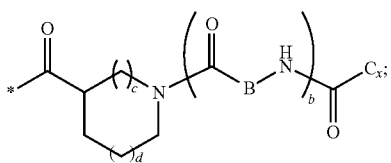

the -* indicate the binding sites of the different groups, that is the co-polyaminoacids, GpR, GpA and GpC, bound by amide functions;
b is an integer equal to 0 or to 1;
p is an integer equal to 2 or 3 and
  if p is equal to 2 then GpA is a radical according to formula III and,
  if p is equal to 3 then GpA is a radical according to formula III';
c is an integer equal to 0 or 1, and if c is 0 then d is 1 or 2;
d is an integer of 0, 1 or 2;
r is an integer equal to 0 or 1, and
  if r is equal to 0, then the hydrophobic radical according to formula I is bound to the co-polyamino acid through a covalent bond between a carbonyl of the co-polyamino acid and a one of the nitrogen atoms of the radical GpA, thereby forming an amide function from the reaction of an amine function, either a primary amine or a secondary amine of the precursor of GpA and an acid function borne by the precursor of the co-polyamino acid, and
  if r is equal to 1 or 2, then the hydrophobic radical according to formula I is bound to the co-polyamino acid:
    through a covalent bond between a nitrogen atom of the radical GpR and a carbonyl of the copoly-amino acid, thus forming an amide function resulting from the reaction of an amine function of the precursor of the radical GpR and an acid function borne by the precursor of the co-polyamino acid or
    through a covalent bond between a carbonyl of the radical GpR and a nitrogen atom in N-terminal position of the co-polyamino acid, thus forming an amide function resulting from the reaction of an acid function of the precursor of the radical GprR and an amine function in N-terminal position borne by the precursor of the co-polyamino acid;
R is a radical chosen from the group consisting of:
  a divalent alkyl radical, linear or branched, comprising from 1 to 11 carbon atoms; and
  a non-substituted ether or polyether radical comprising from 4 to 14 carbon atoms and from 1 to 5 oxygen atoms;

A, A' and A" are identical or different and linear or branched alkyl radicals comprising from 2 to 6 carbon atoms;
B is a linear or branched alkyl radical, optionally comprising an aromatic ring, comprising from 1 to 9 carbon atoms;
$C_x$ is a monovalent alkyl radical, linear or branched, in which x indicates the number of carbon atoms and:
  if p is equal to 2, x is comprised from 9 to 15 ($9 \leq x \leq 15$):
  if p is equal to 3, x is comprised from 7 to 15 ($7 \leq x \leq 15$),
the ratio i between the number of hydrophobic radicals and the number of glutamic or aspartic units being from 0 to 0.5 ($0 < i \leq 0.5$);
when several hydrophobic radicals are carried by a co-polyamino acid they are therefore, identical or different;
the degree of polymerization DP of glutamic or aspartic units is comprised from 5 to 250;
the free acid functions being in the form of an alkaline cation salt chosen from the group consisting of $Na^+$ and $K^+$.

In one embodiment, if GpA is a radical of formula III and r=1, then:
  the GpC are bound to $N^{\alpha 1}$ and $N^{\alpha 2}$ and the copolyamino acid is bound via GpR to $N^{\beta 1}$, or
  the GpC are bound to $N^{\alpha 1}$ and $N^{\beta 1}$, and the co-polyaminoacide is bound via GpR to $N^{\alpha 2}$; or
  the GpC are bound to $N^{\alpha 2}$ and $N^{\beta 1}$, and the copolyamino acid is bound via GpR to $N^{\alpha 1}$.

In one embodiment, if GpA is a radical according to formula III and r=0, then:
  the GpC are bound to $N^{\alpha 1}$ and $N^{\alpha 2}$ and the copolyamino acid is bound to $N^{\beta 1}$; or
  the GpC are bound to $N^{\alpha 1}$ and $N^{\beta 1}$, and the copolyamino acid is bound to $N^{\alpha 2}$; or
  the GpC are bound to $N^{\alpha 2}$ and $N^{\beta 1}$, and the copolyamino acid is bound to $N^{\alpha 1}$.

In one embodiment, if GpA is a radical according to formula III' and r=1, then
  the GpC are bound to $N^{\alpha 1}$, $N^{\alpha 2}$ and $N^{\beta 1}$ and the copolyamino acid is bound via GpR to $N^{\beta 2}$; or
  the GpC are bound to $N^{\alpha 1}$, $N^{\alpha 2}$ and $N^{\beta 2}$ and the copolyamino acid is bound via GpR to $Na^{\beta 1}$; or
  the GpC are bound to $N^{\alpha 1}$, $N^{\beta 1}$ and $N^{\beta 2}$ and the copolyamino acid is bound via GpR to $N^{\alpha 2}$; or
  the GpC are bound to $N^{\alpha 2}$, $N^{\beta 1}$ and $N^{\beta 2}$ and the copolyamino acid is bound via GpR to $N^{\alpha 1}$.

In one embodiment, if GpA is a radical according to formula III' and r=0, then
  the GpC are bound to $N^{\alpha 1}$, $N^{\alpha 2}$ and $N^{\beta 1}$ and the copolyamino acid is bound to $N^{\beta 2}$; or
  the GpC are bound to $N^{\alpha 1}$, $N^{\alpha 2}$ and $N^{\beta 2}$ and the copolyamino acid is bound to $N^{\beta 1}$; or
  the GpC are bound to $N^{\alpha 1}$, $N^{\beta 1}$ and $N^{\beta 2}$ and the copolyamino acid is bound to $N^{\alpha 2}$; or
  the GpC are bound to $N^{\alpha 2}$, $N^{\beta 1}$ and $N^{\beta 2}$ and the copolyamino acid is bound to $N^{\alpha 1}$ The pH of the compositions according to the invention is comprised from 6.0 to 8.0, and preferably from 6.6 to 7.8, or even more preferably, from 6.8 to 7.6.

Said copolyamino acid bearing carboxylate charges and hydrophobic Hy radicals is soluble in an aqueous solution of pH from 6.0 to 8.0, at a temperature of 25° C. and at a concentration of less than 60 mg/ml.

By "physically stable composition" is meant compositions that meet the visual inspection criteria described in European, American and international pharmacopoeia, that is, compositions that are clear and that do not contain visible particles, but are also colorless.

By "injectable aqueous solution" is meant solutions for which the solvent is water and which meet the pharmacopoeia conditions of Europe and the US.

The terms "copolyamino acid consisting of glutamic or aspartic units" refers to non-cyclic linear chains of glutamic acid or aspartic acid units bound together by peptide bonds, said chains having a C-terminal part, corresponding to the carboxylic acid of one extremity, and an N-terminal part, corresponding to the amine of the other extremity of the chain.

The term "soluble" used herein means suitable to prepare a clear, particle-free solution at a concentration below 60 mg/ml in distilled water at 25° C.

The term "alkyl radical" denotes a linear or branched carbon chain, which does not comprise a heteroatom.

Said copolyamino acid is a statistical copolyamino acid in the chain of glutamic and/or aspartic units.

In the formulas, the * indicate the binding sites of the different elements represented.

In one embodiment, the composition according to the invention is characterized in that Hy comprises from 34 to 70 carbon atoms.

In one embodiment, when p=2, x consists of 9 to 15 (9≤x≤15).

In one embodiment, when p=3, x consists of 7 to 15 (7≤x≤15).

In one embodiment, the composition according to the invention is characterized in that the said hydrophobic radicals are selected from the hydrophobic radicals according to formula I are chosen among the hydrophobic radicals according to formula I wherein p=2, represented in the following formula VI:

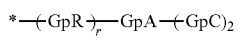

Formula VI dans laquelle GpR, GpA, GpC and r ont les définitions données précédemment.

In one embodiment, the composition according to the invention est caractérisée en ce que le radical hydrophobic is a radical according to formula VI dans laquelle r est égal to 0 (r=0).

In one embodiment, the composition according to the invention is characterized in that the hydrophobic radical is a radical according to formula VI wherein r is equal to 1 (r=1).

In one embodiment, the composition according to the invention is characterized in that the hydrophobic radical is a radical according to formula VI wherein GpR is a radical according to formula II.

In one embodiment, the composition according to the invention is characterized in that the hydrophobic radical is a radical according to formula VI wherein GpR is a radical according to formula II wherein R is a divalent linear alkyl radical consisting of from 1 to 11 carbon atoms.

In one embodiment, the composition according to the invention is characterized in that the hydrophobic radical is a radical according to formula VI wherein GpR is a radical according to formula II wherein R is a divalent alkyl radical consisting of from 1 to 6 carbon atoms.

In one embodiment, the composition according to the invention is characterized in that the hydrophobic radical is a radical according to formula VI wherein GpR is a radical according to formula II wherein R is a radical divalent linear alkyl consisting of from 1 to 6 carbon atoms.

In one embodiment, the composition according to the invention is characterized in that the hydrophobic radical is a radical according to formula VI wherein GpR is a radical according to formula II wherein R is an alkyl radical at least consisting of from 2 to 4 carbon atoms.

In one embodiment, the composition according to the invention is characterized in that the hydrophobic radical is a radical according to formula VI wherein GpR is a radical according to formula II wherein R is a linear alkyl radical divalent consisting of from 2 to 4 carbon atoms.

In one embodiment, the composition according to the invention is characterized in that the hydrophobic radical is a radical according to formula VI wherein GpR is a radical according to formula II wherein R is a divalent linear alkyl radical consisting of 2 carbon atoms.

In one embodiment, the composition according to the invention is characterized in that the hydrophobic radical is a radical according to formula VI wherein GpR is a radical according to formula II'.

In one embodiment, the composition according to the invention is characterized in that the hydrophobic radical is a radical according to formula VI wherein GpR is a radical according to formula II' wherein R is a divalent linear alkyl radical consisting of from 1 to 11 carbon atoms.

In one embodiment, the composition according to the invention is characterized in that the hydrophobic radical is a radical according to formula VI wherein GpR is a radical according to formula II' wherein R is a divalent alkyl radical consisting of from 1 to 6 carbon atoms.

In one embodiment, the composition according to the invention is characterized in that the hydrophobic radical is a radical according to formula VI wherein GpR is a radical according to formula II or II', wherein R is a non-substituted ether or polyether linear radical consisting of from 4 to 14 carbon atoms and from 1 to 5 oxygen atoms.

In one embodiment, the composition according to the invention is characterized in that the hydrophobic radical is a radical according to formula VI wherein GpR is a radical according to formula II or II' wherein R is an ether radical.

In one embodiment, the composition according to the invention is characterized in that the ether radical R is a radical consisting of from 4 to 6 carbon atoms.

In one embodiment, the composition according to the invention is characterized in that the ether radical R is

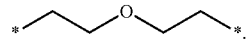

In one embodiment, the composition according to the invention is characterized in that the hydrophobic radical is a radical according to formula VI wherein GpR is a radical according to formula II or II', wherein R is a polyether radical.

In one embodiment, the composition according to the invention is characterized in that the hydrophobic radical is a radical according to formula VI wherein GpR is a radical according to formula II or II', wherein R is a linear polyether radical consisting of from 6 to 10 carbon atoms and from 2 to 3 oxygen atoms.

In one embodiment, the composition according to the invention is characterized in that the hydrophobic radical is a radical according to formula VI wherein GpR is a radical according to formula II or II' wherein R is a linear polyether radical chosen in the group constituted by the radicals represented in the formula below:

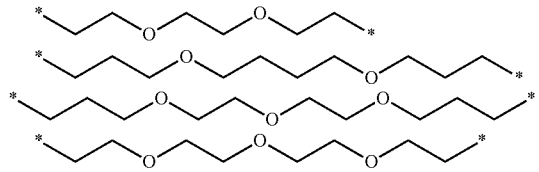

In one embodiment, the composition according to the invention is characterized in that the hydrophobic radical is a radical according to formula VI wherein the radical GpA according to formula III is chosen in the group constituted by the radicals wherein A, A' and A", identical or different, are chosen among the linear alkyl radicals.

In one embodiment, the composition according to the invention is characterized in that the hydrophobic radical is a radical according to formula VI wherein the radical GpA according to formula III is chosen in the group constituted by the radicals wherein A and A', identical or different, are chosen among the linear alkyl radicals consisting of from 3 to 4 carbon atoms.

In one embodiment, the composition according to the invention is characterized in that the hydrophobic radical is a radical according to formula VI wherein the radical GpA according to formula III is chosen in the group constituted by the radicals wherein A and A', identical or different, are chosen among the linear alkyl radicals consisting of from 3 to 4 carbon atoms.

In one embodiment, the composition according to the invention is characterized in that the hydrophobic radical is a radical according to formula VI wherein the radical GpA according to formula III is chosen in the group constituted by the radicals wherein A is chosen among the linear alkyl radicals consisting of 3 carbon atoms and A' is chosen among the linear alkyl radicals consisting of 4 carbon atoms.

In one embodiment, the composition according to the invention is characterized in that the hydrophobic radical is a radical according to formula VI wherein the radical GpA according to formula III is chosen in the group constituted by the radicals wherein A and A', identicals are chosen among the linear alkyl radicals consisting of 3 carbon atoms.

In one embodiment, the composition according to the invention is characterized in that the hydrophobic radical is a radical according to formula VI wherein the radical GpA according to formula III is chosen in the group constituted by the radicals IIIa and IIIb:

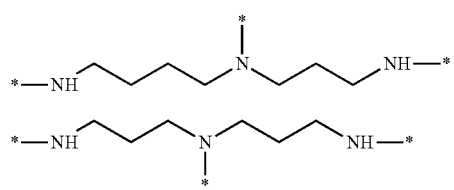

In one embodiment, the composition according to the invention is characterized in that the hydrophobic radical is a radical according to formula VI wherein the radical GpA according to formula III is a radical according to formula IIIa.

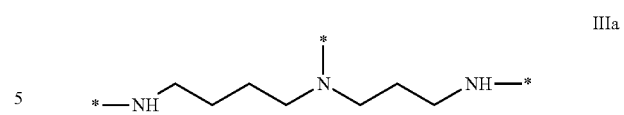

In one embodiment, the composition according to the invention is characterized in that the hydrophobic radical is a radical according to formula VI wherein the radical GpA according to formula III is a radical according to formula IIIb:

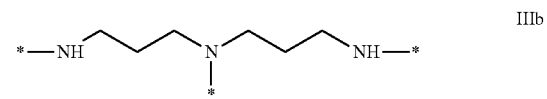 [SMILES: *NCCCN(*)CCCN*]

In one embodiment, the composition according to the invention is characterized in that the hydrophobic radical is a radical according to formula VI wherein the precursor of the radical GpA according to formula III is chosen in the group constituted by triamines consisting of spermidine and the norspermidine.

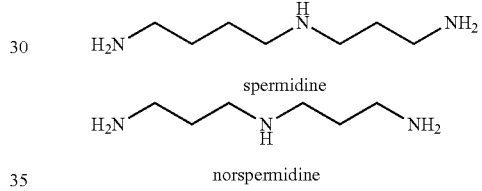

In one embodiment, the composition according to the invention is characterized in that the hydrophobic radical is a radical according to formula VI wherein the precursor of the radical GpA according to formula III is the spermidine.

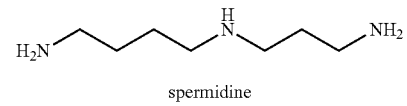

In one embodiment, the composition according to the invention is characterized in that the hydrophobic radical is a radical according to formula VI wherein the precursor of the radical GpA according to formula III is the norspermidine.

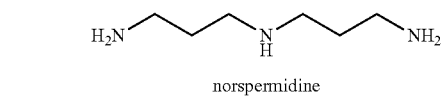

In one embodiment, the composition according to the invention is characterized in that the hydrophobic radical is a radical according to formula VI wherein the radical GpC according to formula IV is chosen in the group constituted by the radicals according to formulas IVa, IVb and IVc ci-après represented:

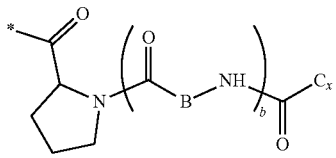

Formula IV$_a$

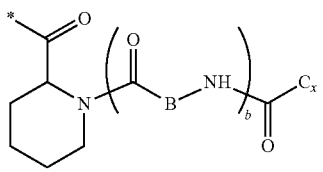

Formula IV$_b$

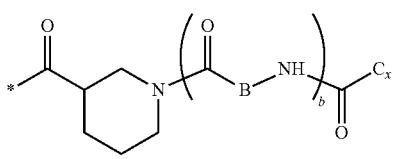

Formula IV$_c$

In one embodiment, the composition according to the invention is characterized in that the hydrophobic radical is a radical according to formula VI wherein the radical GpC is according to formula IVa.

In one embodiment, the composition according to the invention is characterized in that the hydrophobic radical is a radical according to formula VI wherein the radical GpC according to formula IV is chosen in the group constituted by the radicals according to formula IVa, IVb or IVc wherein b is equal to 0, of formulas IVd, IVe, and IVf hereafter represented:

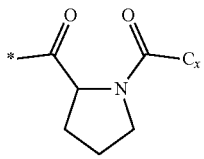

Formula IV$_d$

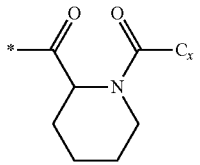

Formula IV$_e$

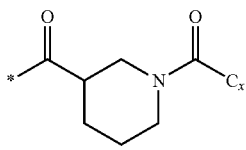

Formula IV$_f$

In one embodiment, the composition according to the invention is characterized in that the hydrophobic radical is a radical according to formula VI wherein the radical GpC according to formula IV or IVa wherein b=0, and has the formula IVd.

In one embodiment, the composition according to the invention is characterized in that the hydrophobic radical is a radical according to formula VI wherein the radical GpC according to formula IV is chosen in the group constituted by the radicals wherein Cx is chosen in the group constituted by the linear alkyl radicals consisting of from 9 to 15 carbon atoms.

In one embodiment, the composition according to the invention is characterized in that the hydrophobic radical is a radical according to formula VI wherein the radical GpC according to formula IV is chosen in the group constituted by the radicals wherein Cx is chosen in the group constituted by the branched alkyl radicals consisting of from 9 to 15 carbon atoms.

In one embodiment, the composition according to the invention is characterized in that the hydrophobic radical is a radical according to formula VI wherein the radical GpC according to formula IV is chosen in the group constituted by the radicals wherein Cx is chosen in the group constituted by the alkyl radicals consisting of from 9 or 10 carbon atoms.

In one embodiment, the composition according to the invention is characterized in that the hydrophobic radical is a radical according to formula VI wherein the radical GpC according to formula IV is chosen in the group constituted by the radicals wherein Cx is chosen in the group constituted by the radicals represented in the formula below:

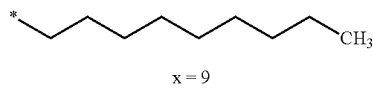

x = 9

In one embodiment, the composition according to the invention is characterized in that the hydrophobic radical is a radical according to formula VI wherein the radical GpC according to formula IV is chosen in the group constituted by the radicals wherein Cx is chosen in the group constituted by the radicals alkyl consisting of from 11 to 15 carbon atoms.

In one embodiment, the composition according to the invention is characterized in that the hydrophobic radical is a radical according to formula VI wherein the radical GpC according to formula IV is chosen in the group constituted by the radicals wherein Cx is chosen in the group constituted by the alkyl radicals consisting of from 11 to 13 carbon atoms.

In one embodiment, the composition according to the invention is characterized in that the hydrophobic radical is a radical according to formula VI wherein the radical GpC according to formula IV is chosen in the group constituted by the radicals wherein Cx is chosen in the group constituted by the radicals represented in the formula below:

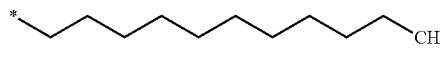

x = 11

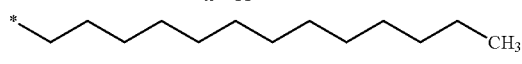

x = 13

In one embodiment, the composition according to the invention is characterized in that the hydrophobic radical is a radical according to formula VI wherein the radical GpC according to formula IV is chosen in the group constituted by the radicals wherein Cx is chosen in the group constituted by the radicals alkyl consisting of 14 or 15 carbon atoms.

In one embodiment, the composition according to the invention is characterized in that the hydrophobic radical is a radical according to formula VI wherein the radical GpC according to formula IV is chosen in the group constituted by the radicals wherein Cx is chosen in the group constituted by the radicals represented in the formula below:

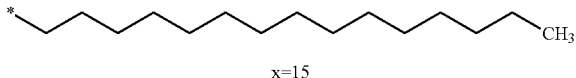 [SMILES: *CCCCCCCCCCCCCCC]

x=15

In the formulas I and VI, the * indicates the binding sites of the hydrophobic radicals to the copolyamino acid. The radicals Hy are bound to the copolyamino acid via amide functions.

In the formulas II and II', the * indicates the binding sites of GpR:
To the copolyamino acid and
to GpA.

In formula III, the * indicates the binding sites of GpA:
to GpR if r=1 or to the copolyamino acid si r=0 and
to GpC.

In one embodiment, when r=0, GpA is bound to the copolyamino acid by a primary amine du radical according to formula III.

In one embodiment, when r=0, GpA is bound to the copolyamino acid by the $N^{\alpha 1}$ primary amine of the radical according to formula III.

In one embodiment, when r=0, GpA is bound to the copolyamino acid by the $N^{\alpha 2}$ primary amine of the radical according to formula III.

In one embodiment, when r=0, GpA is bound to the copolyamino acid by a secondary amine of the radical according to formula III.

In one embodiment, when r=0, GpA is bound to the copolyamino acid by the $N^{\beta 1}$ secondary amine of the radical according to formula III.

In one embodiment, when r=1, GpA is bound to GpR by a $N^{\alpha 1}$ primary amine of the radical according to formula III.

In one embodiment, when r=1, GpA is bound to GpR by the primary amine of the radical according to formula III.

In one embodiment, when r=1, GpA is bound to GpR by the $N^{\alpha 2}$ primary amine of the radical according to formula III.

In one embodiment, when r=1, GpA is bound to GpR by a secondary amine of the radical according to formula III.

In one embodiment, when r=1, GpA is bound to GpR by the $N^{\beta 1}$ secondary amine of the radical according to formula III.

In formula IV, the * indicates the binding sites of GpC to GpA.

All the binding sites between the different groups GpR, GpA and GpC are amides functions.

The radicals Hy, GpR, GpA, GpC, and D are each independently identical or different from one residue to another.

When the copolyamino acid comprises one or several aspartic(s) unit(s), these can undergo structural rearrangements.

In one embodiment, the composition according to the invention is characterized in that said hydrophobic radicals according to formula I are chosen among the hydrophobic radicals according to formula I wherein p=3, represented in the following formula IX:

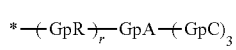

Formula IX wherein GpA is according to formula III' and GpR, GpC, r are as defined above.

In one embodiment, the composition according to the invention is characterized in that the hydrophobic radical is a radical according to formula IX wherein r is equal to 0 (r=0).

In one embodiment, the composition according to the invention is characterized in that the hydrophobic radical is a radical according to formula IX wherein GpR is a radical according to formulas II or II'.

In one embodiment, the composition according to the invention is characterized in that the hydrophobic radical is a radical according to formula IX wherein GpR is a radical according to formulas II or II' wherein R is a divalent linear alkyl radical consisting of from 1 to 11 carbon atoms.

In one embodiment, the composition according to the invention is characterized in that the hydrophobic radical is a radical according to formula IX wherein GpR is a radical according to formulas II or II' wherein R is a divalent alkyl radical consisting of from 1 to 6 carbon atoms.

In one embodiment, the composition according to the invention is characterized in that the hydrophobic radical is a radical according to formula IX wherein GpR is a radical according to formulas II or II' wherein R is a divalent linear alkyl radical consisting of from 1 to 6 carbon atoms.

In one embodiment, the composition according to the invention is characterized in that the hydrophobic radical is a radical according to formula IX wherein GpR is a radical according to formulas II or II' wherein R is an alkyl radical at least consisting of from 2 to 4 carbon atoms.

In one embodiment, the composition according to the invention is characterized in that the hydrophobic radical is a radical according to formula IX wherein GpR is a radical according to formulas II or II' wherein R is a divalent linear alkyl radical consisting of from 2 to 4 carbon atoms.

In one embodiment, the composition according to the invention is characterized in that the hydrophobic radical is a radical according to formula IX wherein GpR is a radical according to formulas II or II' wherein R is a divalent linear alkyl radical consisting of 2 carbon atoms.

In one embodiment, the composition according to the invention is characterized in that the hydrophobic radical is a radical according to formula IX wherein GpR is a radical according to formulas II or II', wherein R is a non-substituted ether or polyether linear radical consisting of from 4 to 14 carbon atoms and of from 1 to 5 oxygen atoms.

In one embodiment, the composition according to the invention is characterized in that the hydrophobic radical is a radical according to formula IX wherein GpR is a radical according to formulas II or II' wherein R is an ether radical.

In one embodiment, the composition according to the invention is characterized in that the ether radical R is a radical consisting of from 4 to 6 carbon atoms.

In one embodiment, the composition according to the invention is characterized in that the ether radical is

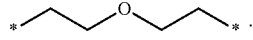

In one embodiment, the composition according to the invention is characterized in that the hydrophobic radical is a radical according to formula IX wherein GpR is a radical according to formulas II or II', wherein R is a polyether radical.

In one embodiment, the composition according to the invention is characterized in that the hydrophobic radical is a radical according to formula IX wherein GpR is a radical according to formulas II or II', wherein R is a linear polyether radical consisting of from 6 to 10 carbon atoms and of from 2 to 3 oxygen atoms.

In one embodiment, the composition according to the invention is characterized in that the hydrophobic radical is a radical according to formula IX wherein GpR is a radical according to formulas II or II' wherein R is a linear polyether radical chosen in the group constituted by the radicals represented in the formulas below:

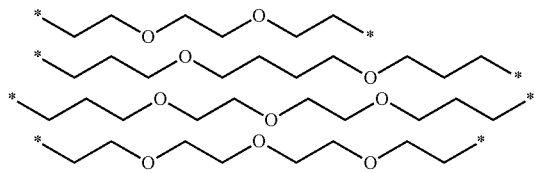

In one embodiment, the composition according to the invention is characterized in that the hydrophobic radical is a radical according to formula IX wherein A, A' and A", identical or different, are chosen among the linear alkyl radicals consisting of from 3 to 4 carbon atoms.

In one embodiment, the composition according to the invention is characterized in that the hydrophobic radical is a radical according to formula IX wherein the radical GpA according to formula III' is chosen in the group constituted by the radicals wherein A and A" identicals are chosen among the linear alkyl radicals consisting of 3 carbon atoms and A' is chosen among the linear alkyl radicals consisting of 4 carbon atoms.

In one embodiment, the composition according to the invention is characterized in that the hydrophobic radical is a radical according to formula VI wherein the radical GpA according to formula III' is a radical according to formula III'a:

III'a

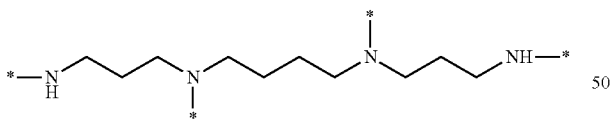

In one embodiment, the composition according to the invention is characterized in that the hydrophobic radical is a radical according to formula VI wherein the precursor of the radical GpA according to formula III' is the spermine:

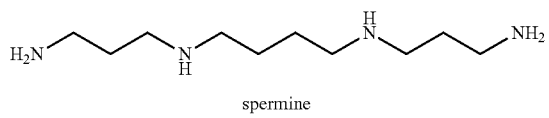 [SMILES: NCCCNCCCCNCCCN]

spermine

In one embodiment, the composition according to the invention is characterized in that the hydrophobic radical is a radical according to formula IX wherein the radical GpC according to formula IV is chosen in the group constituted by the radicals according to formulas IVa, IVb and IVc hereafter represented:

Formula IV$_a$
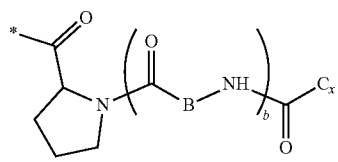

Formula IV$_b$
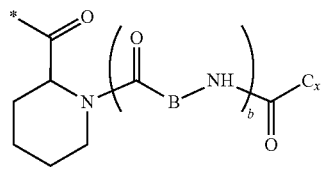

Formula IV$_c$
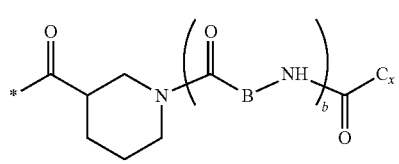

In one embodiment, the composition according to the invention is characterized in that the hydrophobic radical is a radical according to formula IX wherein the radical GpC is according to formula IVa.

In one embodiment, the composition according to the invention is characterized in that the hydrophobic radical is a radical according to formula IX wherein the radical GpC according to formula IV is chosen in the group constituted by the radicals according to formulas IVa, IVb or IVc wherein b is equal to 0, of formulas IVd, IVe, and IVf hereafter represented:

Formula IV$_d$
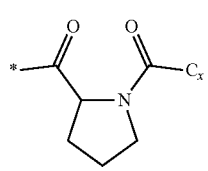

Formula IV$_e$
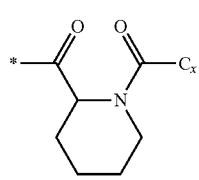

Formula IV$_f$
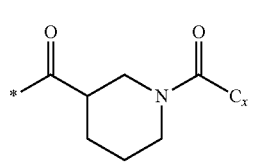

In one embodiment, the composition according to the invention is characterized in that the hydrophobic radical is a radical according to formula IX wherein the radical GpC is according to formula IV or IVa wherein b=0, and has the formula IVd.

In one embodiment, the composition according to the invention is characterized in that the hydrophobic radical is a radical according to formula IX wherein the radical GpC according to formula IV is chosen in the group constituted by the radicals wherein Cx is chosen in the group constituted by the linear alkyl radicals consisting of from 7 to 15 carbon atoms.

In one embodiment, the composition according to the invention is characterized in that the hydrophobic radical is a radical according to formula IX wherein the radical GpC according to formula IV is chosen in the group constituted by the radicals wherein Cx is chosen in the group constituted by the branched alkyl radicals consisting of from 7 to 15 carbon atoms.

In one embodiment, the composition according to the invention is characterized in that the hydrophobic radical is a radical according to formula IX wherein the radical GpC according to formula IV is chosen in the group constituted by the radicals wherein Cx is chosen in the group constituted by the alkyl radicals consisting of 9 or 10 carbon atoms.

In one embodiment, the composition according to the invention is characterized in that the hydrophobic radical is a radical according to formula IX wherein the radical GpC according to formula IV is chosen in the group constituted by the radicals wherein Cx is chosen in the group constituted by the radicals represented in the formula below:

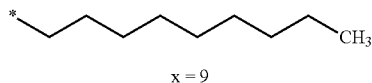

x = 9

In one embodiment, the composition according to the invention is characterized in that the hydrophobic radical is a radical according to formula IX wherein the radical GpC according to formula IV is chosen in the group constituted by the radicals wherein Cx is chosen in the group constituted by the radicals alkyl consisting of from 11 to 15 carbon atoms.

In one embodiment, the composition according to the invention is characterized in that the hydrophobic radical is a radical according to formula IX wherein the radical GpC according to formula IV is chosen in the group constituted by the radicals wherein Cx is chosen in the group constituted by the alkyl radicals consisting of from 11 to 13 carbon atoms.

In one embodiment, the composition according to the invention is characterized in that the hydrophobic radical is a radical according to formula IX wherein the radical GpC according to formula IV is chosen in the group constituted by the radicals wherein Cx is chosen in the group constituted by the radicals represented in the formulas below:

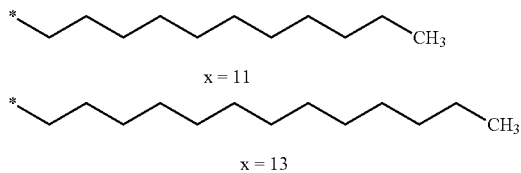

In one embodiment, the composition according to the invention is characterized in that the hydrophobic radical is a radical according to formula IX wherein the radical GpC according to formula IV is chosen in the group constituted by the radicals wherein Cx is chosen in the group constituted by the alkyl radicals consisting of 14 or 15 carbon atoms.

In one embodiment, the composition according to the invention is characterized in that the hydrophobic radical is a radical according to formula IX wherein the radical GpC according to formula IV is chosen in the group constituted by the radicals wherein Cx is chosen in the group constituted by the radicals represented in the formula below:

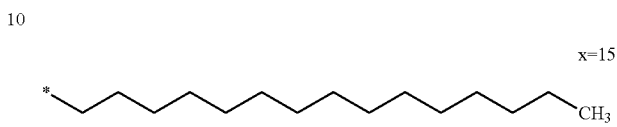

In the formulas I and IX, the -* indicate the binding sites of the hydrophobic radicals to the copolyamino acid.

The radicals Hy are bound to the copolyamino acid via amides functions.

In the formula II and II', the -* indicates the binding sites of GpR:
to the copolyamino acid and
to GpA.

In the formula III', the -* indicates the binding sites of GpA:
to GpR if r=1 or to the copolyamino acid if r=0 and
to GpC.

In one embodiment, when r=0, GpA is bound to the copolyamino acid via a primary amine of the radical according to formula III'.

In one embodiment, when r=0, GpA is bound to the copolyamino acid via the $N^{\alpha 1}$ primary amine of the radical according to formula III'.

In one embodiment, when r=0, GpA is bound to the copolyamino acid via the $N^{\alpha 2}$ primary amine of the radical according to formula III'.

In one embodiment, when r=0, GpA is bound to the copolyamino acid via a secondary amine of the radical according to formula III'.

In one embodiment, when r=0, GpA is bound to the copolyamino acid via the $N^{\beta 1}$ secondary amine of the radical according to formula III'.

In one embodiment, when r=0, GpA is bound to the copolyamino acid via the $N^{\beta 2}$ secondary amine of the radical according to formula III'.

In one embodiment, when r=1, GpA is bound to GpR via a primary amine of the radical according to formula III'.

In one embodiment, when r=1, GpA is bound to GpR via the $N^{\beta 1}$ primary amine of the radical according to formula III'.

In one embodiment, when r=1, GpA is bound to GpR via the $N^{\alpha 2}$ primary amine of the radical according to formula III'.

In one embodiment, when r=1, GpA is bound to GpR via a secondary amine of the radical according to formula III'.

In one embodiment, when r=1, GpA is bound to GpR via the $N^{\alpha 1}$ secondary amine of the radical according to formula III'.

In one embodiment, when r=1, GpA is bound to GpR via the $N^{\alpha 2}$ secondary amine of the radical according to formula III'.

In the formula IV, the * indicates the binding sites of GpC to GpA.

All the binding sites between the different groups GpR, GpA and GpC are amides functions.

The radicals Hy, GpR, GpA, GpC, and D are each independently identical or different from one residue to another.

When the copolyamino acid comprises one or several aspartic(s) unit(s), these can undergo structural rearrangements.

In one embodiment, the composition according to the invention is characterized in that the copolyamino acid bearing carboxylate charges and hydrophobic radicals is chosen among the copolyamino acids according to the following formula VII:

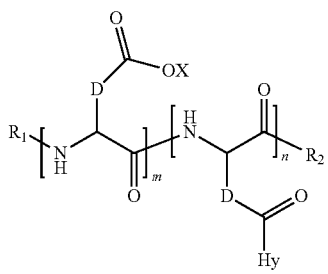

formula VII wherein,
- D is, independently, either a —CH2- group (aspartic unit) or a —CH2-CH2- group (glutamic unit),
- Hy is a hydrophobic radical chosen among the hydrophobic radicals according to formula I, VI or IX,
- $R_1$ is a hydrophobic radical chosen among the hydrophobic radicals according to formula I, VI or IX wherein r=0 or r=1 and GpR is a radical according to formula II, or un radical chosen in the group constituted by a H, a C2 to C10 linear acylated group, a C3 to C10 branched acylated group, a benzyl, a terminal «aminoacid» unit and a pyroglutamate,
- $R_2$ is a hydrophobic radical chosen among the hydrophobic radicals according to formula I, VI or IX wherein r=0 or r=1 and GpR is a radical according to formula II', or a —NR'R", R' and R" identical or different being chosen in the group consisting of H, C2 to C10 linear, branched or cyclic alkyls, benzyl and said R' and R" alkyls may form together one or several saturated, insaturated and/or aromatic carbon rings and/or may include heteroatoms, chosen in the group consisting of O, N and S;
- X is a cationic entity chosen in the group consisting of the alkali metal cations;
- n+m refers to the degree of polymerization DP of the copolyamino acid, that is the mean number of monomeric unit in a copolyamino acid chain and 5≤n+m≤250;

In one embodiment, the composition according to the invention is characterized in that when the copolyamino acid comprises aspartic units, then the copolyamino acid may further comprise monomeric unit according to formula VIII and/or VIII':

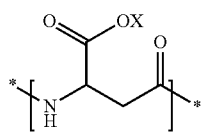

Formula VIII

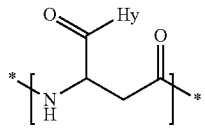

Formula VIII'

The term «random grafting copolyamino acid» refers to a copolyamino acid bearing carboxylate charges and at least a hydrophobic radical, that is a copolyamino acid according to formula VIIa.

In one embodiment, the composition according to the invention is characterized in that the copolyamino acid bearing carboxylate charges and hydrophobic radicals is chosen among the copolyamino acids according to formula VII, wherein $R_1=R'_1$ and $R_2=R'_2$, according to the following formula VIIa:

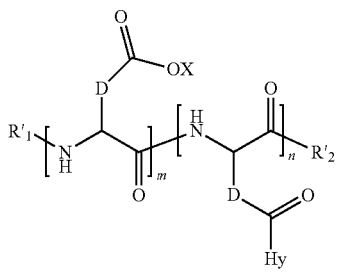

Formula VIIa wherein,
- m, n, X, D and Hy are as defined above,
- $R'_1$ is a radical chosen in the group constituted by H, a C2 to C10 linear acylated group, a C3 to C10 branched acylated group, a benzyl, a terminal «aminoacid» unit and a pyroglutamate,
- $R'_2$ is a radical —NR'R", R' and R" identical or different being chosen in the group consisting of H, C2 to C10 linear, branched or cyclic alkyl and benzyl and said R' and R" alkyls may form together one or several saturated, unsaturated and/or aromatic carbon rings and/or may include heteroatoms, chosen in the group consisting of O, N and S.

The term «grafting defined copolyamino acid» refers to a copolyamino acid bearing carboxylate charges and at least a hydrophobic radical, that is a copolyamino acid according to formula VIIb.

In one embodiment, the composition according to the invention is characterized in that the copolyamino acid bearing carboxylate charges and hydrophobic radicals is chosen among the copolyamino acids according to formula VII wherein n=0 according to formula VIIb suivante:

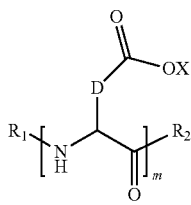

Formula VIIb wherein m, X, D, $R_1$ and $R_2$ are as defined above and at least $R_1$ or $R_2$ is a hydrophobic radical according to formula I, VI or IX.

In one embodiment, the composition according to the invention is characterized in that the copolyamino acid bearing carboxylate charges and hydrophobic radicals is chosen among the copolyamino acids according to formula VII wherein n=0 according to formula VIIb and $R_1$ or $R_2$ is a hydrophobic radical according to formula I, VI or IX.

In one embodiment, the composition according to the invention is characterized in that the copolyamino acid bearing carboxylate charges and hydrophobic radicals is chosen among the copolyamino acids according to formula VIIb wherein $R_1$ is a hydrophobic radical according to formula I, VI or IX wherein r=1 and GpR is according to formula II.

In one embodiment, the composition according to the invention is characterized in that the copolyamino acid bearing carboxylate charges and hydrophobic radicals is chosen among the copolyamino acids according to formula VIIb wherein $R_2$ is a hydrophobic radical according to formula I, VI or IX wherein r=0 or r=1 and GpR is according to formula II'.

In one embodiment, the composition according to the invention is characterized in that $R_1$ is a radical chosen in the group constituted by a C2 to C10 linear acylated group, a C3 to C10 branched acylated group, a benzyl, a terminal «aminoacid» unit and a pyroglutamate.

In one embodiment, the composition according to the invention is characterized in that $R_1$ is a radical chosen in the group constituted by a C2 to C10 linear acylated group or a C3 to C10 branched acylated group.

In one embodiment, the composition according to the invention is characterized in that the copolyamino acid bearing carboxylate charges and hydrophobic radicals is chosen among the copolyamino acids according to formula VII, VIIa or VIIb wherein the copolyamino acid is chosen among the copolyamino acids wherein the group D is a —$CH_2$— group (aspartic unit).

In one embodiment, the composition according to the invention is characterized in that the copolyamino acid bearing carboxylate charges and hydrophobic radicals is chosen among the copolyamino acids according to formula VII, VIIa or VIIb wherein the copolyamino acid is chosen among the copolyamino acids wherein the group D is a —$CH_2$—$CH_2$— group (glutamic unit).

The hydrophobic radical to basal insulin ratio is defined as the ratio of their respective molar concentrations: [Hy]/[insuline basale] (mol/mol) to obtain the expected performances, that is, the solubilization of basal insulin at a pH from 6.0 to 8.0, the precipitation of the basal insulin and the stability of the compositions according to the invention.

The minimum measured value of hydrophobic radical ratio to basal insulin [Hy]/[insuline basale], is the value to for which the basal insulin is solubilized, as the solubilization is the minimum effect to be obtained; this solubilization is a condition to all other technical effects that can only be observed if the basal insulin is solubilized to a pH comprised of from 6.0 to 8.0.

In the compositions according to the invention, the hydrophobic radical to basal insulin ratio [Hy]/[insuline basale] may be superior to the minimum value determined by the solubilisation limit.

In one embodiment, the hydrophobic radical to basal insulin ratio [Hy]/[insuline basale]≤2.

In one embodiment, the hydrophobic radical to basal insulin ratio [Hy]/[insuline basale]≤1.75.

In one embodiment, the hydrophobic radical to basal insulin ratio [Hy]/[insuline basale]≤1.5.

In one embodiment, the hydrophobic radical to basal insulin ratio [Hy]/[insuline basale]≤1.25.

In one embodiment, the hydrophobic radical to basal insulin ratio [Hy]/[insuline basale]≤1.00.

In one embodiment, the hydrophobic radical to basal insulin ratio [Hy]/[insuline basale]≤0.75.

In one embodiment, the hydrophobic radical to basal insulin ratio [Hy]/[insuline basale]≤0.5.

In one embodiment, the hydrophobic radical to basal insulin ratio [Hy]/[insuline basale]≤0.25.

In one embodiment, the composition according to the invention is characterized in that the ratio i between the hydrophobic radicals number and the glutamic or aspartic units number consists of from 0.007 to 0.3.

In one embodiment, the composition according to the invention is characterized in that the ratio i between the hydrophobic radicals number and the glutamic or aspartic units number consists of from 0.01 to 0.3.

In one embodiment, the composition according to the invention is characterized in that the ratio i between the hydrophobic radicals number and the glutamic or aspartic units number consists of from 0.02 to 0.2.

In one embodiment, the composition according to the invention is characterized in that the hydrophobic radical is according to formula VI and the ratio i between the hydrophobic radicals number and the glutamic or aspartic units number consists of from 0.007 to 0.15.

In one embodiment, the composition according to the invention is characterized in that the hydrophobic radical is according to formula VI and the ratio i between the hydrophobic radicals number and the glutamic or aspartic units number consists of from 0.01 to 0.1.

In one embodiment, the composition according to the invention is characterized in that the hydrophobic radical is according to formula VI and the ratio i between the hydrophobic radicals number and the glutamic or aspartic units number consists of from 0.02 to 0.08.

In one embodiment, the composition according to the invention is characterized in that the hydrophobic radical is according to formula VI wherein the radical Cx comprises de 9 to 10 carbon atoms and the ratio i between the hydrophobic radicals number and the glutamic or aspartic units number consists of from 0.03 to 0.15.

In one embodiment, the composition according to the invention is characterized in that the hydrophobic radical is according to formula VI wherein the radical Cx comprises de 11 to 12 carbon atoms and the ratio i between the hydrophobic radicals number and the glutamic or aspartic units number consists of from 0.015 to 0.1.

In one embodiment, the composition according to the invention is characterized in that the hydrophobic radical is according to formula VI wherein the radical Cx comprises de 11 to 12 carbon atoms and the ratio i between the hydrophobic radicals number and the glutamic or aspartic units number consists of from 0.02 to 0.08.

In one embodiment, the composition according to the invention is characterized in that the hydrophobic radical is according to formula VI wherein the radical Cx comprises de 13 to 15 carbon atoms and the ratio i between the hydrophobic radicals number and the glutamic or aspartic units number consists of from 0.01 to 0.1.

In one embodiment, the composition according to the invention is characterized in that the hydrophobic radical is according to formula VI wherein the radical Cx comprises de 13 to 15 carbon atoms and the ratio i between the hydrophobic radicals number and the glutamic or aspartic units number consists of from 0.01 to 0.06.

In one embodiment, the composition according to the invention is characterized in that the hydrophobic radical is according to formula IX and the ratio i between the hydrophobic radicals number and the glutamic or aspartic units number consists of from 0.007 to 0.15.

In one embodiment, the composition according to the invention is characterized in that the hydrophobic radical is according to formula IX and the ratio i between the hydrophobic radicals number and the glutamic or aspartic units number consists of from 0.01 to 0.1.

In one embodiment, the composition according to the invention is characterized in that the hydrophobic radical is according to formula IX and the ratio i between the hydrophobic radicals number and the glutamic or aspartic units number consists of from 0.02 to 0.08.

In one embodiment, the composition according to the invention is characterized in that the hydrophobic radical is according to formula IX wherein the radical Cx consists of from 7 and 10 carbon atoms and the ratio i between the hydrophobic radicals number and the glutamic or aspartic units number consists of from 0.03 to 0.15.

In one embodiment, the composition according to the invention is characterized in that the hydrophobic radical is according to formula IX wherein the radical Cx consists of from 11 to 12 carbon atoms and the ratio i between the hydrophobic radicals number and the glutamic or aspartic units number consists of from 0.015 to 0.1.

In one embodiment, the composition according to the invention is characterized in that the hydrophobic radical is according to formula IX wherein the radical Cx consists of from 11 to 12 carbon atoms and the ratio i between the hydrophobic radicals number and the glutamic or aspartic units number consists of from 0.02 to 0.08.

In one embodiment, the composition according to the invention is characterized in that the hydrophobic radical is according to formula IX wherein the radical Cx consists of from 13 to 15 carbon atoms and the ratio i between the hydrophobic radicals number and the glutamic or aspartic units number consists of from 0.01 to 0.1.

In one embodiment, the composition according to the invention is characterized in that the hydrophobic radical is according to formula IX wherein the radical Cx consists of from 13 to 15 carbon atoms and the ratio i between the hydrophobic radicals number and the glutamic or aspartic units number consists of from 0.01 to 0.06.

In one embodiment, the composition according to the invention is characterized in that n+m consists of from 10 to 200.

In one embodiment, the composition according to the invention is characterized in that n+m consists of from 15 to 150.

In one embodiment, the composition according to the invention is characterized in that n+m is comprised from 15 to 100.

In one embodiment, the composition according to the invention is characterized in that n+m consists of from 15 to 80.

In one embodiment, the composition according to the invention is characterized in that n+m consists of from 15 to 65.

In one embodiment, the composition according to the invention is characterized in that n+m consists of from 20 to 60.

In one embodiment, the composition according to the invention is characterized in that n+m consists of from 20 to 50.

In one embodiment, the composition according to the invention is characterized in that n+m consists of from 20 to 40.

The invention also relates to said copolyamino acids bearing carboxylate charges and hydrophobic radicals according to formula I, VI or IX.

In one embodiment, the invention also relates to the precursors of said hydrophobic radicals according to formulas I', VI' and IX':

H-(GpR)$_r$-GpA-(GpC)$_p$            Formula I'

H-(GpR)$_r$-GpA-(GpC)$_2$            Formula VI'

H-(GpR)$_r$-GpA-(GpC)$_3$            Formula IX'

GpR, GpA, GpC, r and p are as defined above.

The invention also relates to a method of preparation of stable injectable compositions.

In one embodiment, the copolyamino acid bearing carboxylate charges and hydrophobic radicals is a copolyamino acid according to formula VII or VIIb, wherein DP=27, 0.028≤i≤0.045 and the at least un hydrophobic radical is according to formula I is chosen among the radicals according to formula I wherein r=0, p=2, GpA is according to formula Ma, GpC is according to formula IVd wherein x

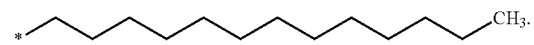 [SMILES: *CCCCCCCCCCCCC]

=13 and Cx is

In one embodiment, the copolyamino acid bearing carboxylate charges and hydrophobic radicals is un copolyamino acid according to formula VII or VIIa, wherein DP=22, 0.023≤i≤0.04 and the at least un hydrophobic radical is according to formula I is chosen among the radicals according to formula I wherein r=0, p=2, GpA is according to formula Ma, R2 or R'2 is the hexylamine, GpC is according to formula IVd wherein x=13 and Cx is

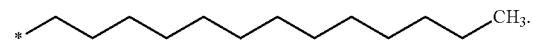 [SMILES: *CCCCCCCCCCCCC]

In one embodiment, the copolyamino acid bearing carboxylate charges and hydrophobic radicals is un copolyamino acid according to formula VII or VIIa, wherein DP=22, 0.036≤i≤0.046 and the at least a hydrophobic radical is according to formula I is chosen among the radicals according to formula I wherein r=0, p=2, GpA is according to formula Ma, R2 or R'2 is the hexylamine, GpC is according to formula IVd wherein x=11 and Cx is

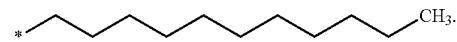 [SMILES: *CCCCCCCCCCC]

In one embodiment, the copolyamino acid bearing carboxylate charges and hydrophobic radicals is a copolyamino acid according to formula VII or VIIb, wherein DP=22, 0.040≤i≤0.050 and the at least a hydrophobic radical is according to formula I is chosen among the radicals according to formula I wherein r=0, p=2, GpA is according to formula IIIb, GpC is according to formula IVd wherein x=13 and Cx is

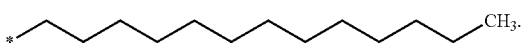 [SMILES: *CCCCCCCCCCCCC]

In one embodiment, the composition according to the invention is characterized in that the copolyamino acid is obtained from a polyaminoacid obtained via polymerization.

In one embodiment, the composition according to the invention is characterized in that the copolyamino acid is obtained from a polyaminoacid obtained via polymerization by ring-opening of a N-carboxyanhydride glutamic acid derivative or a N-carboxyanhydride aspartic acid derivative.

In one embodiment, the composition according to the invention is characterized in that the copolyamino acid is obtained from a polyaminoacid obtained via polymerization of a N-carboxyanhydride glutamic acid derivative or a N-carboxyanhydride aspartic acid derivative as described in the article Adv. Polym. Sci. 2006, 202, 1-18 (Deming, T. J.).

In one embodiment, the composition according to the invention is characterized in that the copolyamino acid is obtained from a polyaminoacid obtained via polymerization of a N-carboxyanhydride glutamic acid derivative.

In one embodiment, the composition according to the invention is characterized in that the copolyamino acid is obtained from a polyaminoacid obtained via polymerization of a N-carboxyanhydride glutamic acid derivative chosen in the group constituted by the N-carboxyanhydride methyl polyglutamate (GluOMe-NCA), the N-carboxyanhydride benzyl polyglutamate (GluOBzl-NCA) and the N-carboxyanhydride tert-butyle polyglutamate (GluOtBu-NCA).

In one embodiment, the N-carboxyanhydride glutamic acid derivative is the N-carboxyanhydride methyl poly-L-glutamate (L-GluOMe-NCA).

In one embodiment, the N-carboxyanhydride glutamic acid derivative is the benzyl N-carboxyanhydride poly-L-glutamate (L-GluOBzl-NCA).

In one embodiment, the composition according to the invention is characterized in that the copolyamino acid is obtained from a polyaminoacid obtained via polymerization of a N-carboxyanhydride glutamic acid derivative or a N-carboxyanhydride aspartic acid derivative using a transition metal organometallic complexe as initiator as described in Nature 1997, 390, 386-389 (Deming, T. J.).

In one embodiment, the composition according to the invention is characterized in that the copolyamino acid is obtained from a polyaminoacid obtained via polymerization of a N-carboxyanhydride glutamic acid derivative or a N-carboxyanhydride aspartic acid derivative using ammonia or a primary amine as initiator as described in patent FR 2,801,226 (Torraud, F.; and al.) and the references cited in this patent.

In one embodiment, the composition according to the invention is characterized in that the copolyamino acid is obtained from a polyaminoacid obtained via polymerization of a N-carboxyanhydride glutamic acid derivative or a N-carboxyanhydride aspartic acid derivative using the hexamethyldisilazane as initiator as described in the article J. Am. Chem. Soc. 2007, 129, 14114-14115 (Lu H.; and al.) or a silylated amine as described in the article J. Am. Chem. Soc. 2008, 130, 12562-12563 (Lu H.; and al.).

In one embodiment, the composition according to the invention is characterized in that the process for synthesizing the polyaminoacid obtained via polymerization of a N-carboxyanhydride glutamic acid derivative or a N-carboxyanhydride aspartic acid derivative from which the copolyamino acid is obtained comprises a step of ester function hydrolysis.

In one embodiment, this ester function hydrolysis step may consist of hydrolysis in an acidic medium or hydrolysis in a basic medium or may be carried out by hydrogenation.

In one embodiment, this ester group hydrolysis step is a hydrolysis in an acidic medium.

In one embodiment, this ester group hydrolysis step is carried out by hydrogenation.

In one embodiment, the composition according to the invention is characterized in that the copolyamino acid is obtained from a polyaminoacid obtained via depolymerization of a polyamino acid of higher molecular weight.

In one embodiment, the composition according to the invention is characterized in that the copolyamino acid is obtained from a polyaminoacid obtained via enzymatic depolymerization of a polyamino acid of higher molecular weight.

In one embodiment, the composition according to the invention is characterized in that the copolyamino acid is obtained from a polyaminoacid obtained by chemical depolymerization of a polyamino acid of higher molecular weight.

In one embodiment, the composition according to the invention is characterized in that the copolyamino acid is obtained from a polyaminoacid obtained by enzymatic and chemical depolymerization of a polyamino acid of higher molecular weight.

In one embodiment, the composition according to the invention is characterized in that the copolyamino acid is obtained from a polyaminoacid obtained via depolymerization of a polyamino acid of higher molecular weight chosen in the group constituted by sodium polyglutamate and sodium polyaspartate.

In one embodiment, the composition according to the invention is characterized in that the copolyamino acid is obtained from a polyaminoacid obtained by depolymerization of sodium polyglutamate of higher molecular weight.

In one embodiment, the composition according to the invention is characterized in that the copolyamino acid is obtained from a polyaminoacid obtained by depolymerization sodium polyaspartate of higher molecular weight.

In one embodiment, the composition according to the invention is characterized in that the copolyamino acid is obtained by grafting a hydrophobic group onto an acid poly-L-glutamic acid or poly-L-aspartic acid using amide bond-forming methods well known to those skilled in the ar.

In one embodiment, the composition according to the invention is characterized in that the copolyamino acid is obtained by grafting a hydrophobic group onto a poly-L-glutamic acid or poly-L-aspartic acid using amide bond formation processes used for peptide synthesis.

In one embodiment, the composition according to the invention is characterized in that the copolyamino acid is obtained by grafting a hydrophobic group onto a poly-L-glutamic acid or poly-L-aspartic acid as described in patent FR 2,840,614 (Chan, Y. P.; and al.).

Hereinafter, the units used for insulins are those recommended by pharmacopoeias, whose mg/ml equivalences are provided in the table hereafter:

| Insuline | Pharmacopée EP 8.0 (2014) | Pharmacopée US - USP38 (2015) |
|---|---|---|
| Aspart | 1U = 0.0350 mg of insulin aspart | 1 USP = 0.0350 mg of insulin aspart |
| Lispro | 1U = 0.0347 mg of insulin lispro | 1 USP = 0.0347 mg of insulin lispro |

| Insuline | Pharmacopée EP 8.0 (2014) | Pharmacopée US - USP38 (2015) |
| --- | --- | --- |
| Humaine | 1UI = 0.0347 mg of insulin humaine | 1 USP = 0.0347 mg of insulin humaine |
| Glargine | 1U = 0.0364 mg of insulin glargine | 1 USP = 0.0364 mg of insulin glargine |
| Porcine | 1UI = 0.0345 mg of insulin porcine | 1 USP = 0.0345 mg of insulin porcine |
| Bovine | 1UI = 0.0342 mg of insulin bovine | 1 USP = 0.0342 mg of insulin bovine |

By basal insulin with an isoelectric point from 5.8 to 8.5 is meant an insoluble insulin at pH 7 and whose duration of action is comprised from 8 to 24 hours or longer in standard diabetes models.

These basal insulins, whose isoelectric point is comprised from 5.8 to 8.5, are recombinant insulins whose primary structure has been modified mainly by introducing basic amino acids such as Arginine or Lysine. They are described, for example, in the following patents, patent applications or publications: WO 2003/053339, WO 2004/096854, U.S. Pat. Nos. 5,656,722 and 6,100,376, the content of which is incorporated by reference.

In one embodiment, the basal insulin with an isoelectric point from 5.8 to 8.5 is insulin glargine. Insulin glargine is marketed under the brand Lantus® (100 U/ml) or Toujeo® (300 U/ml) by SANOFI.

In one embodiment, the basal insulin with an isoelectric point from 5.8 to 8.5 is a bio-similar insulin glargine.

Bio-similar insulin glargine is being marketed under the brand Abasaglar® or Basaglar® by ELI LILLY.

In one embodiment, the compositions according to the invention comprise from 40 to 500 U/mL of basal insulin for which the isoelectric point is comprised from 5.8 to 8.5.

In one embodiment, the compositions according to the invention comprise 40 U/mL of basal insulin for which the isoelectric point is comprised from 5.8 to 8.5.

In one embodiment, the compositions according to the invention comprise 100 U/mL (that is about 3.6 mg/mL) of basal insulin for which the isoelectric point is comprised from 5.8 to 8.5.

In one embodiment, the compositions according to the invention comprise 150 U/mL of basal insulin for which the isoelectric point is comprised from 5.8 to 8.5.

In one embodiment, the compositions according to the invention comprise 200 U/mL of basal insulin for which the isoelectric point is comprised from 5.8 to 8.5.

In one embodiment, the compositions according to the invention comprise 225 U/mL of basal insulin for which the isoelectric point is comprised from 5.8 to 8.5.

In one embodiment, the compositions according to the invention comprise 250 U/mL of basal insulin for which the isoelectric point is comprised from 5.8 to 8.5.

In one embodiment, the compositions according to the invention comprise 300 U/mL of basal insulin for which the isoelectric point is comprised from 5.8 to 8.5.

In one embodiment, the compositions according to the invention comprise 400 U/mL of basal insulin for which the isoelectric point is comprised from 5.8 to 8.5.

In one embodiment, the compositions according to the invention comprise 500 U/mL of basal insulin for which the isoelectric point is comprised from 5.8 to 8.5.

In one embodiment, the mass ratio between the basal insulin, for which the isoelectric point is comprised from 5.8 to 8.5, and the copolyamino acid, or copolyamino acid/basal insulin, is comprised from 0.2 to 8.

In one embodiment, the mass ratio is comprised from 0.2 to 6.

In one embodiment, the mass ratio is comprised from 0.2 to 5.

In one embodiment, the mass ratio is comprised from 0.2 to 4.

In one embodiment, the mass ratio is comprised from 0.2 to 3.

In one embodiment, the mass ratio is comprised from 0.2 to 2.

In one embodiment, the mass ratio is comprised from 0.2 to 1.

In one embodiment, the concentration in copolyamino acid bearing carboxylate charges and hydrophobic radicals is at most 60 mg/mL.

In one embodiment, the concentration in copolyamino acid bearing carboxylate charges and hydrophobic radicals is at most 40 mg/mL.

In one embodiment, the concentration in copolyamino acid bearing carboxylate charges and hydrophobic radicals is at most 20 mg/mL.

In one embodiment, the concentration in copolyamino acid bearing carboxylate charges and hydrophobic radicals is at most 10 mg/mL.

In one embodiment, the concentration in copolyamino acid bearing carboxylate charges and hydrophobic radicals is at most 5 mg/ml.

In one embodiment, the concentration in copolyamino acid bearing carboxylate charges and hydrophobic radicals is at most 2.5 mg/ml.

In one embodiment, the compositions according to the invention comprise furthermore a prandial insulin. The prandial insulins are soluble at pH 7.

Prandial insulin means a so-called rapid or "regular" insulin.

So-called rapid prandial insulins are insulins which must respond to the needs caused by the ingestion of proteins and sugars during a meal; they must act in less than 30 minutes.

In one embodiment, the so-called "regular" prandial insulin is human insulin.

In one embodiment, the prandial insulin is a recombinant human insulin as described in European Pharmacopeia and American Pharmacopeia.

Human insulin is marketed, for example, under the brands Humulin® (ELI LILLY) and Novolin® (NOVO NORDISK).

So-called fast acting prandial insulins are insulins which are obtained by recombination and whose primary structure has been modified to decrease their acting time.

In one embodiment, so-called fast acting prandial insulins are chosen from the group comprising insulin lispro (Humalog®), insulin glulisine (Apidra®) and insulin aspart (NovoLog®).

In one embodiment, the prandial insulin is insulin lispro.

In one embodiment, the prandial insulin is insulin glulisine.

In one embodiment, the prandial insulin is insulin aspart.

In one embodiment, the compositions according to the invention comprise in total de 60 to 800 U/mL of insulin with a combination of prandial insulin and basal insulin for which the isoelectric point is comprised from 5.8 to 8.5.

In one embodiment, the compositions according to the invention comprise in total de 100 to 500 U/mL of insulin with a combination of prandial insulin and basal insulin for which the isoelectric point is comprised from 5.8 to 8.5.

In one embodiment, the compositions according to the invention comprise in total 800 U/mL of insulin with a combination of prandial insulin and basal insulin for which the isoelectric point is comprised from 5.8 to 8.5.

In one embodiment, the compositions according to the invention comprise in total 700 U/mL of insulin with a combination of prandial insulin and basal insulin for which the isoelectric point is comprised from 5.8 to 8.5.

In one embodiment, the compositions according to the invention comprise in total 600 U/mL of insulin with a combination of prandial insulin and basal insulin for which the isoelectric point is comprised from 5.8 to 8.5.

In one embodiment, the compositions according to the invention comprise in total 500 U/mL of insulin with a combination of prandial insulin and basal insulin for which the isoelectric point is comprised from 5.8 to 8.5.

In one embodiment, the compositions according to the invention comprise in total 400 U/mL of insulin with a combination of prandial insulin and basal insulin for which the isoelectric point is comprised from 5.8 to 8.5.

In one embodiment, the compositions according to the invention comprise in total 300 U/mL of insulin with a combination of prandial insulin and basal insulin for which the isoelectric point is comprised from 5.8 to 8.5.

In one embodiment, the compositions according to the invention comprise in total 266 U/mL of insulin with a combination of prandial insulin and basal insulin for which the isoelectric point is comprised from 5.8 to 8.5.

In one embodiment, the compositions according to the invention comprise in total 200 U/mL of insulin with a combination of prandial insulin and basal insulin for which the isoelectric point is comprised from 5.8 to 8.5.

In one embodiment, the compositions according to the invention comprise in total 100 U/mL of insulin with a combination of prandial insulin and basal insulin for which the isoelectric point is comprised from 5.8 to 8.5.

The proportions between the basal insulin for which the isoelectric point is comprised from 5.8 to 8.5 and the prandial insulin are for example in percentage of from 25/75, 30/70, 40/60, 50/50, 60/40, 63/37, 70/30, 75/25, 80/20, 83/17, 90/10 for formulations as described above consisting of from 60 to 800 U/mL. However, any other proportion can be achieved.

In one embodiment, the compositions according to the invention further comprise a gastrointestinal hormone.

By "gastrointestinal hormones" is meant hormones chosen from the group consisting of GLP-1 RA (Glucagon-like peptide-1 receptor agonist) and GIP (Glucose-dependent insulinotropic peptide), oxyntomodulin (a derivative of proglucagon), YY peptide, amylin, cholecystokinin, pancreatic peptide (PP), ghrelin and enterostatin, their analogues or derivatives and/or their pharmaceutically acceptable salts.

In one embodiment, the gastrointestinal hormones are analogues or derivatives of GLP-1 RA chosen from the group consisting of exenatide or Byetta® (ASTRA-ZENECA), liraglutide or Victoza® (NOVO NORDISK), lixisenatide or Lyxumia® (SANOFI), albiglutide or Tanzeum® (GSK) or dulaglutide or Trulicity® (ELI LILLY & CO), their analogues or derivatives and/or their pharmaceutically acceptable salts.

In one embodiment, the gastrointestinal hormone is pramlintide or Symlin® (ASTRA-ZENECA).

In one embodiment, the gastrointestinal hormone is exenatide or Byetta®, its analogues or derivatives and their pharmaceutically acceptable salts.

In one embodiment, the gastrointestinal hormone is liraglutide or Victoza®, its analogues or derivatives and their pharmaceutically acceptable salts.

In one embodiment, the gastrointestinal hormone is lixisenatide or Lyxumia®, its analogues or derivatives and their pharmaceutically acceptable salts.

In one embodiment, the gastrointestinal hormone is albiglutide or Tanzeum®, its analogues or derivatives and their pharmaceutically acceptable salts.

In one embodiment, the gastrointestinal hormone is dulaglutide or Trulicity®, its analogues or derivatives and their pharmaceutically acceptable salts.

In one embodiment, the gastrointestinal hormone is pramlintide or Symlin®, its analogues or derivatives and their pharmaceutically acceptable salts.

The term "analog" means, when used with reference to a peptide or a protein, a peptide or a protein, which one or a plurality of its constituent amino acid residues have been substituted by other amino acid residues and/or which one or a plurality of its constituent amino acid residues have been removed and/or which one or a plurality of its constituent amino acid residues have been added. The percentage of homology allowed for the present definition of an analog is 50%.

The term "derivative" means, when used with reference to a peptide or a protein, a peptide or a protein or an analog chemically modified by a substituent which is not present in the reference peptide or protein or analog, i.e. a peptide or a protein which has been modified by creating covalent bonds, to introduce substituents.

In one embodiment, the substituent is chosen from the group consisting of fatty chains.

In one embodiment, the concentration of gastrointestinal hormone is comprised within a range from 0.01 to 100 mg/mL.

In one embodiment, the concentration of exenatide, its analogues or derivatives and their pharmaceutical acceptable salts is comprised within a range from 0.04 to 0.5 mg/mL.

In one embodiment, the concentration of liraglutide, its analogues or derivatives and their pharmaceutical acceptable salts is comprised within a range from 1 to 10 mg/mL.

In one embodiment, the concentration of lixisenatide, its analogues or derivatives and their pharmaceutical acceptable salts is comprised within a range from 0.01 to 1 mg/mL.

In one embodiment, the concentration of albiglutide, its analogues or derivatives and their pharmaceutical acceptable salts is comprised from 5 to 100 mg/mL.

In one embodiment, the concentration of dulaglutide, its analogues or derivatives and their pharmaceutical acceptable salts is comprised from 0.1 to 10 mg/mL.

In one embodiment, the concentration of pramlintide, its analogues or derivatives and their pharmaceutical acceptable salts is comprised from 0.1 to 5 mg/mL.

In one embodiment, the compositions according to the invention are obtained by mixing commercial solutions of basal insulin which isoelectric point is from 5.8 to 8.5 and commercial solutions of GLP-1 RA, analogue or derivative of GLP-1 RA in volume ratios within a range from 10/90 to 90/10.

In one embodiment, the compositions according to the invention are obtained from basal insulin for which the isoelectric point is comprised from 5.8 to 8.5 in powder.

In one embodiment, the compositions according to the invention are obtained by mixing concentrated solutions of basal insulin for which the isoelectric point is comprised from 5.8 to 8.5 and prandial insulin prepared from said insulins in powder.

In one embodiment, the basal insulin in powder for which the isoelectric point is comprised from 5.8 to 8.5 is a bio-similar insulin glargine (Gan & Lee Pharmaceutical).

In one embodiment, the prandial insulin in powder is insulin lispro (Gan & Lee Pharmaceutical).

In one embodiment, the composition according to the invention comprises a daily dose of basal insulin and a daily dose of gastrointestinal hormone.

In one embodiment, the compositions according to the invention comprise from 40 U/mL to 500 U/mL of basal insulin for which the isoelectric point is comprised from 5.8 to 8.5 and, from 0.05 to 0.5 mg/mL of exenatide.

In one embodiment, the compositions according to the invention comprise from 40 U/mL to 500 U/mL of basal insulin for which the isoelectric point is comprised from 5.8 to 8.5 and, of 1 to 10 mg/mL of liraglutide.

In one embodiment, the compositions according to the invention comprise from 40 U/mL to 500 U/mL of basal insulin for which the isoelectric point is comprised from 5.8 to 8.5 and, of 0.01 to 1 mg/mL of lixisenatide.

In one embodiment, the compositions according to the invention comprise from 40 U/mL to 500 U/mL of basal insulin for which the isoelectric point is comprised from 5.8 to 8.5 and, of 5 to 100 mg/mL of albiglutide.

In one embodiment, the compositions according to the invention comprise from 40 U/mL to 500 U/mL of basal insulin for which the isoelectric point is comprised from 5.8 to 8.5 and, of 0.1 to 10 mg/mL of dulaglutide.

In one embodiment, the compositions according to the invention comprise 500 U/mL of basal insulin for which the isoelectric point is comprised from 5.8 to 8.5 and, of 0.04 to 0.5 mg/mL of exenatide.

In one embodiment, the compositions according to the invention comprise 500 U/mL of basal insulin for which the isoelectric point is comprised from 5.8 to 8.5 and, of 1 to 10 mg/mL of liraglutide.

In one embodiment, the compositions according to the invention comprise 500 U/mL of basal insulin for which the isoelectric point is comprised from 5.8 to 8.5 and, of 0.01 to 1 mg/mL of lixisenatide.

In one embodiment, the compositions according to the invention comprise 500 U/mL of basal insulin for which the isoelectric point is comprised from 5.8 to 8.5 and, of 5 to 100 mg/mL of albiglutide.

In one embodiment, the compositions according to the invention comprise 500 U/mL of basal insulin for which the isoelectric point is comprised from 5.8 to 8.5 and, of 0.1 to 10 mg/mL of dulaglutide.

In one embodiment, the compositions according to the invention comprise 400 U/mL of basal insulin for which the isoelectric point is comprised from 5.8 to 8.5 and, of 0.04 to 0.5 mg/mL of exenatide.

In one embodiment, the compositions according to the invention comprise 400 U/mL of basal insulin for which the isoelectric point is comprised from 5.8 to 8.5 and, of 1 to 10 mg/mL of liraglutide.

In one embodiment, the compositions according to the invention comprise 400 U/mL of basal insulin for which the isoelectric point is comprised from 5.8 to 8.5 and, of 0.01 to 1 mg/mL of lixisenatide.

In one embodiment, the compositions according to the invention comprise 400 U/mL of basal insulin for which the isoelectric point is comprised from 5.8 to 8.5 and, of 5 to 100 mg/mL of albiglutide.

In one embodiment, the compositions according to the invention comprise 400 U/mL of basal insulin for which the isoelectric point is comprised from 5.8 to 8.5 and, of 0.1 to 10 mg/mL of dulaglutide.

In one embodiment, the compositions according to the invention comprise 300 U/mL of basal insulin for which the isoelectric point is comprised from 5.8 to 8.5 and, of 0.04 to 0.5 mg/mL of exenatide.

In one embodiment, the compositions according to the invention comprise 300 U/mL of basal insulin for which the isoelectric point is comprised from 5.8 to 8.5 and, of 1 to 10 mg/mL of liraglutide.

In one embodiment, the compositions according to the invention comprise 300 U/mL of basal insulin for which the isoelectric point is comprised from 5.8 to 8.5 and, of 0.01 to 1 mg/mL of lixisenatide.

In one embodiment, the compositions according to the invention comprise 300 U/mL of basal insulin for which the isoelectric point is comprised from 5.8 to 8.5 and, of 5 to 100 mg/mL of albiglutide.

In one embodiment, the compositions according to the invention comprise 300 U/mL of basal insulin for which the isoelectric point is comprised from 5.8 to 8.5 and, of 0.1 to 10 mg/mL of dulaglutide.

In one embodiment, the compositions according to the invention comprise 225 U/mL of basal insulin for which the isoelectric point is comprised from 5.8 to 8.5 and, of 0.04 to 0.5 mg/mL of exenatide.

In one embodiment, the compositions according to the invention comprise 225 U/mL of basal insulin for which the isoelectric point is comprised from 5.8 to 8.5 and, of 1 to 10 mg/mL of liraglutide.

In one embodiment, the compositions according to the invention comprise 225 U/mL of basal insulin for which the isoelectric point is comprised from 5.8 to 8.5 and, of 0.01 to 1 mg/mL of lixisenatide.

In one embodiment, the compositions according to the invention comprise 225 U/mL of basal insulin for which the isoelectric point is comprised from 5.8 to 8.5 and, of 5 to 100 mg/mL of albiglutide.

In one embodiment, the compositions according to the invention comprise 225 U/mL of basal insulin for which the isoelectric point is comprised from 5.8 to 8.5 and, of 0.1 to 10 mg/mL of dulaglutide.

In one embodiment, the compositions according to the invention comprise 200 U/mL of basal insulin for which the isoelectric point is comprised from 5.8 to 8.5 and, of 0.04 to 0.5 mg/mL of exenatide.

In one embodiment, the compositions according to the invention comprise 200 U/mL of basal insulin for which the isoelectric point is comprised from 5.8 to 8.5 and, of 1 to 10 mg/mL of liraglutide.

In one embodiment, the compositions according to the invention comprise 200 U/mL of basal insulin for which the isoelectric point is comprised from 5.8 to 8.5 and, of 0.01 to 1 mg/mL of lixisenatide.

In one embodiment, the compositions according to the invention comprise 200 U/mL of basal insulin for which the isoelectric point is comprised from 5.8 to 8.5 and, of 5 to 100 mg/mL of albiglutide.

In one embodiment, the compositions according to the invention comprise 200 U/mL of basal insulin for which the isoelectric point is comprised from 5.8 to 8.5 and, of 0.1 to 10 mg/mL of dulaglutide.

In one embodiment, the compositions according to the invention comprise 100 U/mL (that is about 3.6 mg/mL) of basal insulin for which the isoelectric point is comprised from 5.8 to 8.5 and, of 0.04 to 0.5 mg/mL of exenatide.

In one embodiment, the compositions according to the invention comprise 100 U/mL (that is about 3.6 mg/mL) of basal insulin for which the isoelectric point is comprised from 5.8 to 8.5 and, of 1 to 10 mg/mL of liraglutide.

In one embodiment, the compositions according to the invention comprise 100 U/mL (that is about 3.6 mg/mL) of basal insulin for which the isoelectric point is comprised from 5.8 to 8.5 and, of 0.01 to 1 mg/mL of lixisenatide.

In one embodiment, the compositions according to the invention comprise 100 U/mL of basal insulin for which the isoelectric point is comprised from 5.8 to 8.5 and, of 5 to 100 mg/mL of albiglutide.

In one embodiment, the compositions according to the invention comprise 100 U/mL of basal insulin for which the isoelectric point is comprised from 5.8 to 8.5 and, of 0.1 to 10 mg/mL of dulaglutide.

In one embodiment, the compositions according to the invention comprise 40 U/mL of basal insulin for which the isoelectric point is comprised from 5.8 to 8.5 and, of 0.04 to 0.5 mg/mL of exenatide.

In one embodiment, the compositions according to the invention comprise 40 U/mL of basal insulin for which the isoelectric point is comprised from 5.8 to 8.5 and, of 1 to 10 mg/mL of liraglutide.

In one embodiment, the compositions according to the invention comprise 40 U/mL of basal insulin for which the isoelectric point is comprised from 5.8 to 8.5 and, of 0.01 to 1 mg/mL of lixisenatide.

In one embodiment, the compositions according to the invention comprise 40 U/mL of basal insulin for which the isoelectric point is comprised from 5.8 to 8.5 and, of 5 to 100 mg/mL of albiglutide.

In one embodiment, the compositions according to the invention comprise 40 U/mL of basal insulin for which the isoelectric point is comprised from 5.8 to 8.5 and, of 0.1 to 10 mg/mL of dulaglutide.

In one embodiment, the compositions according to the invention further comprise zinc salts in a concentration comprised from 0 to 5000 µM.

In one embodiment, the compositions according to the invention further comprise zinc salts in a concentration comprised from 0 to 4000 µM.

In one embodiment, the compositions according to the invention further comprise zinc salts in a concentration comprised from 0 to 3000 µM.

In one embodiment, the compositions according to the invention further comprise zinc salts in a concentration comprised from 0 to 2000 µM.

In one embodiment, the compositions according to the invention further comprise zinc salts in a concentration comprised from 0 to 1000 µM.

In one embodiment, the compositions according to the invention further comprise zinc salts in a concentration comprised from 50 to 600 µM.

In one embodiment, the compositions according to the invention further comprise zinc salts in a concentration comprised from 100 to 500 µM.

In one embodiment, the compositions according to the invention further comprise zinc salts in a concentration comprised from 200 to 500 µM.

In one embodiment, the compositions according to the invention further comprise buffers.

In one embodiment, the compositions according to the invention comprise buffers in concentrations comprise from 0 to 100 mM.

In one embodiment, the compositions according to the invention comprise buffers in concentrations comprise from 15 to 50 mM.

In one embodiment, the compositions according to the invention comprise a buffer chosen in the group consisting of a phosphate buffer, Tris (trishydroxymethylaminomethane) and sodium citrate.

In one embodiment, the buffer is sodium phosphate.

In one embodiment, the buffer is Tris (trishydroxymethylaminomethane).

In one embodiment, the buffer is sodium citrate.

In one embodiment, the compositions according to the invention further comprise preservatives.

In one embodiment, preservatives are chosen in the group consisting of m-cresol and phenol, alone or in mixture.

In one embodiment, the concentration of preservatives is comprised from 10 to 50 mM.

In one embodiment, the concentration of preservatives is comprised from 10 to 40 mM.

In one embodiment, the compositions according to the invention further comprise a surfactant.

In one embodiment, the surfactant is chosen in the group consisting of propylene glycol and polysorbate.

The compositions according to the invention may further comprise additives such as tonicity agents.

In one embodiment, tonicity agents are chosen in the group consisting of glycerine, sodium chloride, mannitol and glycine.

The compositions according to the invention may further comprise all excipients compliant with pharmacopoeias and compatible with the insulins used in standard concentrations.

The invention also relates to a pharmaceutical formulation according to the invention, characterized in that it is obtained by drying and/or lyophilization.

In the case of local and systemic releases, suitable administration routes are intravenous, subcutaneous, intradermal or intramuscular.

Transdermal, oral, nasal, vaginal, ocular, oral and pulmonary routes of administration are also considered.

The invention also relates to single-dose formulations at pH from 6.0 to 8.0 comprising a basal insulin which isoelectric point is from 5.8 to 8.5.

The invention also relates to single-dose formulations at pH from 6.0 to 8.0 comprising a basal insulin which isoelectric point is from 5.8 to 8.5 and a prandial insulin.

The invention also relates to single-dose formulations at pH from 6.0 to 8.0 comprising a basal insulin which isoelectric point is from 5.8 to 8.5 and a gastrointestinal hormone, as defined above.

The invention also relates to single-dose formulations at pH from 6.0 to 8.0 comprising a basal insulin which isoelectric point is from 5.8 to 8.5, a prandial insulin and a gastrointestinal hormone, as defined above.

The invention also relates to single-dose formulations at pH from 6.6 to 7.8 consisting of a basal insulin for which the isoelectric point is comprised from 5.8 to 8.5.

The invention also relates to single-dose formulations at pH from 6.6 to 7.8 consisting of a basal insulin for which the isoelectric point is comprised from 5.8 to 8.5.

The invention also relates to single-dose formulations at pH from 6.6 to 7.8 consisting of a basal insulin for which the isoelectric point is comprised from 5.8 to 8.5 and a gastrointestinal hormone, as defined above.

The invention also relates to single-dose formulations at pH from 6.6 to 7.8 consisting of a basal insulin for which the isoelectric point is comprised from 5.8 to 8.5, a prandial insulin and a gastrointestinal hormone, as defined above.

The invention also relates to single-dose formulations at pH from 6.6 to 7.6 consisting of a basal insulin for which the isoelectric point is comprised from 5.8 to 8.5.

The invention also relates to single-dose formulations at pH from 6.6 to 7.6 consisting of a basal insulin for which the isoelectric point is comprised from 5.8 to 8.5 and a prandial insulin.

The invention also relates to single-dose formulations at pH from 6.6 to 7.6 consisting of a basal insulin for which the isoelectric point is comprised from 5.8 to 8.5 and a gastrointestinal hormone, as defined above.

The invention also relates to single-dose formulations at pH from 6.6 to 7.6 consisting of a basal insulin for which the isoelectric point is comprised from 5.8 to 8.5, a prandial insulin and a gastrointestinal hormone, as defined above.

In one embodiment, the single-dose formulations further comprise a copolyamino acid as defined above.

In one embodiment, the formulations are in injectable solution form.

In one embodiment, the basal insulin for which the isoelectric point is comprised from 5.8 to 8.5 is insulin glargine.

In one embodiment, the prandial insulin is human insulin.

In one embodiment, insulin is a human insulin recombinante telle que décrite dans la Pharmacopée Européenne and la Pharmacopée américaine.

In one embodiment, the prandial insulin is chosen in the group consisting of insulin lispro (Humalog®), insulin glulisine (Apidra®) and insulin aspart (NovoLog®).

In one embodiment, the prandial insulin is insulin lispro.

In one embodiment, the prandial insulin is insulin glulisine.

In one embodiment, the prandial insulin is insulin aspart.

In one embodiment, le GLP-1 RA, analogue or derive de GLP-1 RA is chosen in the group consisting of exenatide (Byetta®), liraglutide (Victoza®), lixisenatide (Lyxumia®), albiglutide (Tanzeum®), dulaglutide (Trulicity®) or one of their derivatives.

In one embodiment, the gastrointestinal hormone is exenatide.

In one embodiment, the gastrointestinal hormone is liraglutide.

In one embodiment, the gastrointestinal hormone is lixisenatide.

In one embodiment, the gastrointestinal hormone is albiglutide.

In one embodiment, the gastrointestinal hormone is dulaglutide.

The solubilization at pH from 6.0 to 8.0 of the basal insulins which isoelectric point is from 5.8 to 8.5, by the copolyamino acids bearing carboxylate charges and at least one hydrophobic radical according to the invention, may be observed and controlled simply, with the naked eye, by means of a change of appearance of the solution.

The solubilization at pH from 6.6 to 7.8 of the basal insulins which isoelectric point is from 5.8 to 8.5, by the copolyamino acids bearing carboxylate charges and at least one hydrophobic radical according to the invention, may be observed and controlled simply, with the naked eye, by means of a change of appearance of the solution.

Furthermore, and just as importantly, the applicant has been able to verify that a basal insulin whose isoelectric point is comprised from 5.8 to 8.5, solubilized at a pH from 6.0 to 8.0 in the presence of a copolyamino acid bearing carboxylate charges and at least one hydrophobic radical according to the invention, preserves its slow-acting insulin action, whether alone or in combination with a prandial insulin or a gastrointestinal hormone.

The applicant was also able to verify that a prandial insulin mixed at pH from 6.0 to 8.0 in the presence of a copolyamino acid bearing carboxylate charges and at least one hydrophobic radical according to the invention and a basal insulin whose isoelectric point is comprised from 5.8 to 8.5, preserves its rapid-release insulin action It is advantageously possible to prepare a composition according to the invention by simply mixing an aqueous solution of basal insulin whose isoelectric point is comprised from 5.8 to 8.5 and a copolyamino acid bearing carboxylate charges and at least one hydrophobic radical according to the invention, in aqueous solution or in lyophilized form. If necessary, the pH of the preparation is adjusted to a pH from 6.0 to 8.0.

It is advantageously possible to prepare a composition according to the invention by simply mixing an aqueous solution of basal insulin whose isoelectric point is comprised from 5.8 to 8.5 and a solution of prandial insulin, and a copolyamino acid bearing carboxylate charges and at least one hydrophobic radical according to the invention, in aqueous solution or in lyophilized form. If necessary, the pH of the preparation is adjusted to a pH from 6.0 to 8.0.

It is advantageously possible to prepare a composition according to the invention by simply mixing an aqueous solution of basal insulin whose isoelectric point is comprised from 5.8 to 8.5, and a solution of GLP-1 RA, an analog or derivative of GLP-1 RA and a co-polyamino acid bearing carboxylate charges and at least one hydrophobic radical according to the invention, in aqueous solution or in lyophilized form. If necessary, the pH of the preparation is adjusted to a pH from 6.0 to 8.0.

It is advantageously possible to prepare a composition according to the invention by simply mixing an aqueous solution of basal insulin whose isoelectric point is comprised from 5.8 to 8.5 and a solution of prandial insulin, and a solution of GLP-1 RA or an analogue or derivative of GLP-1 RA, and a co-polyamino acid bearing carboxylate charges and at least one hydrophobic radical according to the invention, in aqueous solution or in lyophilized form. If necessary, the pH of the preparation is adjusted to a pH from 6.0 to 8.0.

In one embodiment, the mixture of basal insulin and co-polyamino acid is concentrated by ultrafiltration before mixing with the prandial insulin in aqueous solution or in lyophilized form.

If necessary, the composition of the mixture is adjusted with excipients such as glycerine, m-cresol, zinc chloride and polysorbate (Tween®) by addition of concentrated solutions of these excipients to the mixture. If necessary, the pH of the preparation is adjusted to a pH from 6.0 to 8.0.

FIG. 1: FIG. 1 depicts the glycemia average curves in percent of deviation with respect to the basal level±standard error of the average after simultaneous and separated administrations of insulin lispro (Humalog®—example C1) (100 IU/mL, 0.17 IU/kg) and of insulin glargine (Lantus®—example C4) (100 IU/mL, 0.50 U/kg) (filled circles) and of composition CB3-1 (266 U/ml, 0.67 U/kg) (empty squares); administrations have been carried out on dogs (n=10), by subcutaneous injection, and on the x-axis is the post-injection time (in hours) and y-axis the glucose level (in % of deviation with respect to the basal level).

EXAMPLES

The invention is described in more details with the following examples in a non-limited manner.

Part A—Synthesis of Hydrophobic Molecules

The structures of hydrophobic molecules are represented in Table 1.

TABLE 1

List of hydrophobic molecules Hyd.

| Molecule | Structures |
|---|---|
| A1 | 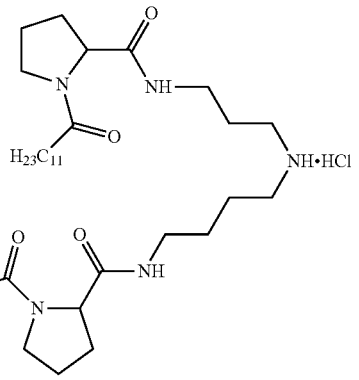 |
| A2 | 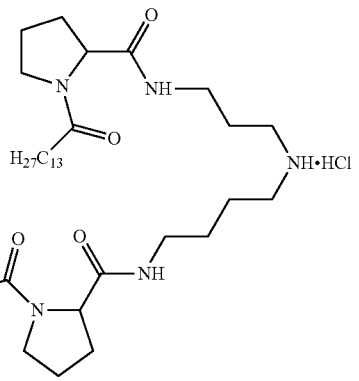 |

TABLE 1-continued

List of hydrophobic molecules Hyd.

| Molecule | Structures |
|---|---|
| A4 | 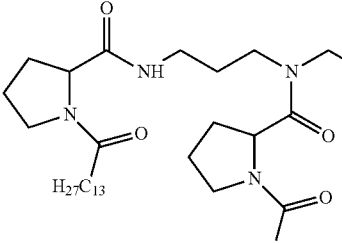 |

Example A1: Molecule A1

Molecule 1
Product Obtained by Coupling Between Lauric Acid and L-Proline

To a solution of dodecanoïc acid (19.77 g, 98.70 mmol) in THF (1 L) are successively added dicyclohexyl carbodiimide (DCC) (20.77 g, 100.68 mmol) and N-hydroxysuccinimide (NHS) (11.59 g, 100.68 mmol). After stirring for 24 h at room temperature, the medium is cooled down to 0° C. and filtered on frit. L-proline (12.50 g, 108.57 mmol), diisopropylethylamine (DIPEA) (63.78 g, 493.51 mmol) and water (90 mL) are added to the filtrate. After stirring for 24 h to room temperature, the medium is concentrated under reduced pressure, then dissolved into water (300 mL). The aqueous phase is washed with ethyl acetate (2×400 mL), acidified until pH ~1 with a 1 N HCl aqueous solution then extracted with dichloromethane (3×250 mL). The combined organic phases are dried over Na2SO4, filtered off, and concentrated under reduced pressure. Après purification by chromatography on silica gel (cyclohexane, ethyl acetate), a colourless oil of molecule 1 is obtained. Yield: 20.53 g (70%)

NMR $^1$H (CDCl$_3$, ppm): 0.87 (3H); 1.26 (16H); 1.70 (2H); 1.90-2.10 (3H); 2.35 (2H); 2.49 (1H); 3.48 (1H); 3.56 (1H); 4.60 (1H)

LC/MS (ESI): 298.2; (calculé ([M+H]$^+$): 298.3)

Molecule 2
Product Obtained by Coupling Between Molecule 1 and Spermidine

To a solution of molecule 1 (20.48 g, 68.85 mmol) to 0° C. in dichloromethane (DCM, 340 mL) is added 1,1'-carbonyldiimidazole (CDI) (11.05 g, 68.16 mmol) and the reaction medium is stirred at room temperature over 1.5 h. Spermidine (5.41 mL, 34.42 mmol) is added and the mixture is stirred over 20 h. The solution is introduced into water, the phases are separated then the aqueous phase is extracted twice with dichloromethane. The combined organic phases are dried over Na2SO4, filtered, concentrated under vacuum and the residue is purified by gel chromatography on silica (dichloromethane, 7 N ammonia in methanol). The product obtained which is contaminated with imidazole, is solubilized in dichloromethane and washed successively with a NaHCO$_3$ saturated aqueous solution (twice) then water (twice). The organic phase is dried over Na2SO4, filtered, and concentrated under vacuum to give a yellowish oil.
Yield: 17.0 g (70%)

NMR $^1$H (DMSO-d6, ppm): 0.85 (6H); 1.10-1.55 (42H); 1.71-2.03 (8H); 2.08-2.29 (4H); 2.43-2.52 (4H); 2.97-3.16 (4H); 3.20-3.57 (5H); 4.16-4.28 (2H); 7.62-8.09 (2H)

LC/MS (ESI): 704.7; (calculated ([M+H]$^+$): 704.6)

Molecule A1

To a solution of de molecule 2 (17.0 g, 24.14 mmol) in dichloromethane (120 mL) is added a 4 N chlorhydric acid solution in dioxane (12.07 mmol, 48.29 mmol) at 0° C. The reaction medium is stirred at room temperature over 1 h, then concentrated under reduced pressure. The residue is solubilized in methanol and concentrated under vacuum. The residue is triturated in acetonitrile, filtered, washed with acetonitrile and dried under reduced pressure at 50° C. The molecule A1 is obtained as a white solid.

Yield: 12.39 g (69%)

NMR $^1$H (DMSO, ppm): 0.85 (6H); 1.08-1.63 (40H); 1.70-2.33 (14H); 2.78-2.88 (4H); 3.00-3.18 (4H); 3.31-3.59 (4H); 4.12-4.34 (2H); 7.77-8.32 (2H); 8.60-8.90 (2H) LC/MS (ESI): 704.8; (calculated ([M+H]$^+$): 704.6)

Example A2: Molecule A2

Molecule 3
Product Obtained by Coupling Between Myristic Acid and L-Proline

Using a similar process than the one used for preparing molecule 1 applied to myristic acid (18.03 g, 78.96 mmol) and to L-proline (10.00 g, 86.86 mmol), a colourless oil of molecule 3 is obtained.

Yield: 17.66 g (69%)

NMR $^1$H (CDCl$_3$, ppm): 0.88 (3H); 1.28 (20H); 1.70 (2H); 1.90-2.10 (3H); 2.36 (2H); 2.51 (1H); 3.47 (1H); 3.56 (1H); 4.61 (1H) LC/MS (ESI): 326.4; (calculated ([M+H]$^+$): 326.3)

Molecule 4
Product Obtained by Coupling Between La Molecule 3 and La Spermidine

To a solution of molecule 3 (17.41 g, 53.50 mmol) at 0° C. in dichloromethane (260 mL) is added 1,1'-carbonyl-diimidazole (CDI) (8.67 g, 53.50 mmol) and the reaction medium is stirred at room temperature over 1.5 h. Spermidine (4.20 mL, 26.75 mmol) is added and the mixture is stirred over 20 h. The reaction medium is washed 4 times with a 0.2 M NaHCO$_3$ aqueous solution, dried over Na$_2$SO$_4$, filtered, and concentrated under vacuum to give a yellowish solid.

Yield: 20.2 g (99%)

NMR $^1$H (DMSO-d6, ppm): 0.85 (6H); 1.09-2.30 (62H); 2.45-2.56 (4H); 2.96-3.56 (8H); 3.98-4.28 (2H); 7.69-8.14 (2H) LC/MS (ESI): 761.0; (calculated ([M+H]$^+$): 760.7)

Molecule A2

Using a similar process than the one used for preparing molecule A1 applied to molecule 4 (20.21 g, 26.59 mmol), a white solid is obtained after recrystallization in acetonitrile.

Yield: 16.3 g (77%)

NMR $^1$H (DMSO-d6, ppm): 0.86 (6H); 1.08-2.36 (62H); 2.78-2.89 (4H); 3.02-3.18 (4H); 3.34-3.61 (4H); 4.14-4.32 (2H); 7.80-8.31 (2H); 8.60-8.88 (2H)

LC/MS (ESI): 760.9; (calculated ([M+H]$^+$): 760.7)

Example A4: Molecule A4

Molecule 6
Product Obtained by Reacting Norspermidine and Di-Tert-Butyl Dicarbonate To a solution of norspermidine (99.2 g, 0.756 mol) in THF (1.1 L) to 0° C. is added di-tert-butyl dicarbonate (55.0 g, 0.252 mol) in THF (715 mL) dropwise over 2.5 h. After stirring for 24 h at 0° C., le solvent is evaporated under reduced pressure. The residue is taken up into water (600 mL) and the product is extracted with dichloromethane (7×500 mL). The combined organic phases are washed with a saturated NaCl aqueous solution (500 mL), dried over Na2SO4 and concentrated under reduced pressure. La molecule 6 is obtained as a colourless oil and used without further purification.

Molecule 7
Product Obtained by Coupling Between La Molecule 3 and La Molecule 6

To a solution of molecule 3 (20.68 g, 63.50 mmol) and molecule 6 (7.0 g, 30.30 mmol) in DMF (70 mL) at 0° C. are successively added DIPEA (15.64 g, 121 mmol) and 1-[Bis(dimethylamino)methylene]-1H-1,2,3-triazolo[4,5-b]pyridinium 3-oxide hexafluorophosphate (HATU, 25.31 g, 66.60 mmol). The reaction mixture is stirred over 24 h with the temperature being risen until 25° C., then the mixture is introduced into iced water (700 mL). The product is extracted with ethyl acetate (300 mL), the organic phase is washed with a 1 N HCl aqueous solution (300 mL), a saturated sodium bicarbonate aqueous solution (300 mL), a saturated NaCl aqueous solution (500 mL), dried over Na$_2$SO$_4$ and concentrated under reduced pressure. A pale yellow oil of molecule 7 is obtained after three successive purifications by flash chromatography (eluents: DCM/MeOH, AcOEt/3% MeOH in DCM, DCM/MeOH).

Yield: 18.9 g (74%)

NMR $^1$H (CDCl$_3$, ppm): 0.87 (6H); 1.15-2.42 (69H); 2.79-3.83 (12H); 4.17-4.31 (0.5H); 4.46-4.65 (0.5H); 4.69-4.83 (0.5H); 5.19-5.30 (0.5H); 5.32-5.42 (0.5H); 5.95-6.08 (0.5H); 7.59-7.76 (0.5H); 7.98-8.14 (0.5H)

LC/MS (ESI): 746.53, 846.60; (calculated ([M+H-Boc]$^+$): 746.65 ([M+H]$^+$): 846.70)

Molecule A4

To a solution of molecule 7 (15.82 g, 18.70 mmol) in dichloromethane (52 mL) at 0° C. is added a 5.7 N HCl solution in dioxane (16.4 mL, 93.50 mmol). After 48 h at 0° C., the reaction mixture is concentrated under reduced pressure. The residue is dissolved into dichloromethane (90 mL), cooled down at 0° C. and washed with an 1 N iced soda solution (2×75 mL) then a saturated NaCl aqueous solution (50 mL). After drying over Na$_2$SO$_4$, a spatula of activated charcoal is introduced, the medium is stirred over 30 minutes then filtered over celite. The molecule A4 is obtained after concentration under reduced pressure.

Yield: 12.40 g (89%).

NMR $^1$H (CDCl$_3$, ppm): 0.87 (6H); 1.08-2.47 (62H); 2.50-3.92 (12H); 4.16-4.33 (0.5H); 4.40-4.62 (0.5H); 4.70-4.88 (0.5H); 5.25-5.39 (0.5H); 7.53-7.77 (0.5H); 7.98-8.28 (0.5H)

LC/MS (ESI): 746.55; (calculated ([M+H]$^+$): 746.65)

Part B—Synthesis of Grafted Copolyamino Acids with Hydrophobic Molecules

The structures of hydrophobic copolyamino acids are represented in Table 2.

TABLE 2 list and structures of grafted copolyamino acids with hydrophobic molecules Hy.

| Copolyamino acid | Structure |
|---|---|
| B1 | 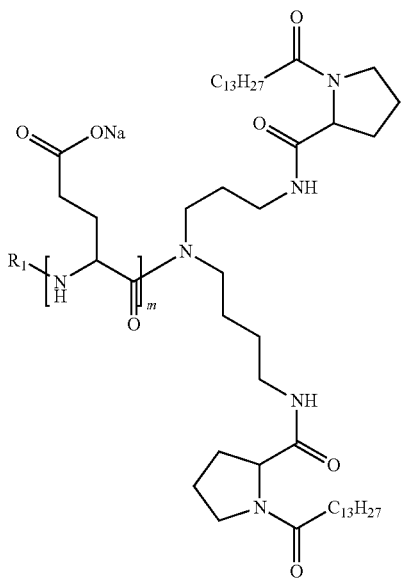<br>i = 0.037, DP (m) = 27<br>$R_1$ = H or pyroglutamate |
| B2 | 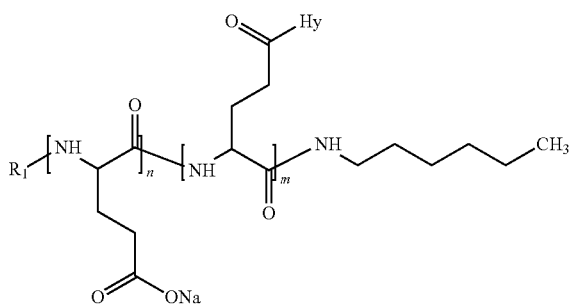<br>i = 0.032, DP = 22<br><br>Hy = 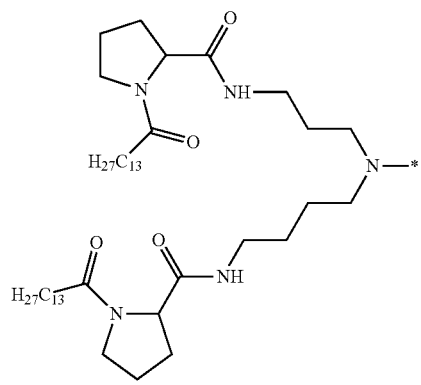<br>$R_1$ = H, $CH_3CO—$ or pyroglutamate |

TABLE 2-continued
list and structures of grafted copolyamino acids with hydrophobic molecules Hy.
| Copolyamino acid | Structure |
| --- | --- |
| B3 | 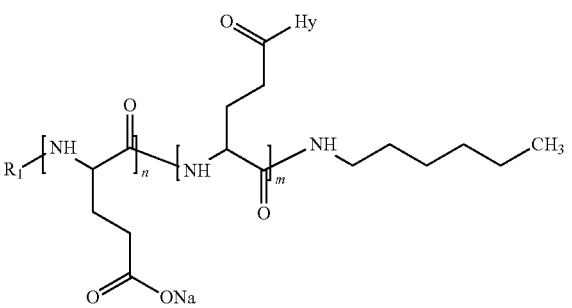 |
$i = 0.041$ DP = 22
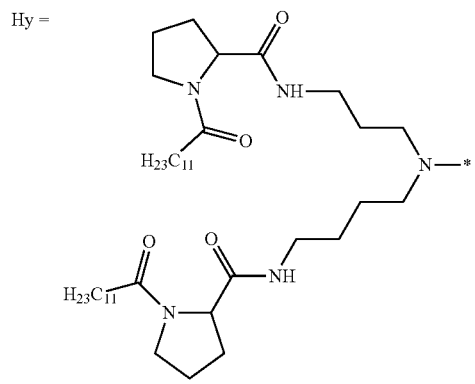
$R_1$ = H or pyroglutamate
| B4 | 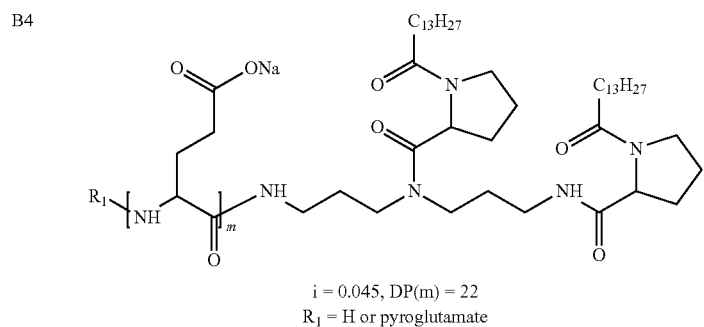 |
$i = 0.045$, DP(m) = 22
$R_1$ = H or pyroglutamate

Example B1: Copolyamino Acid B1-Sodium Poly-L-Glutamate Modified at One of its Extremities with Molecule A2 with Number-Average Molecular Weight (Mn) of 3650 g/Mol Molecule 5:
Product Obtained by Coupling Between Molecule A2 and the N-Hydroxysuccinimic Ester of N-Boc-γ-Tert-Butyl-L-Glutamate (BocGlu(OtBu)OSu)

To a solution of BocGlu(OtBu)OSu (1.81 g, 4.52 mmol) in 30 mL of chloroform is added a solution of molecule A2 (3 g, 3.77 mmol) and N,N-diisopropylethylamine (DIPEA, 0.49 g, 3.77 mmol) in 8 mL of chloroform. After stirring for 18 h at room temperature, the organic phase is washed with water (75 mL) then with a saturated NaCl aqueous solution (5×80 mL), dried over $Na_2SO_4$, filtered and concentrated under reduced pressure. Molecule 5 is obtained after purification by flash chromatography (eluent: AcOEt/MeOH).

Yield: 0.92 g (23%)

NMR $^1H$ (CDCl$_3$, ppm): 0.88 (6H); 1.15-2.44 (84H); 2.91-3.85 (12H); 4.25-4.75 (3H); 5.16-5.39 (1H); 7.28-7.72 (2H)

LC/MS (ESI): 1046.0; (calculated ([M+H]$^+$): 1045.8)
Molecule 6:

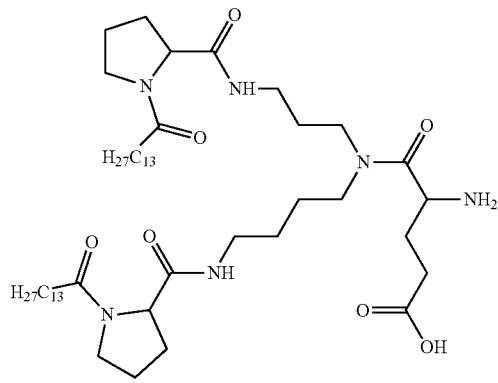

To a solution of Molecule 5 (0.92 g, 0.88 mmol) in 10 mL of dichloromethane is added a 4 N HCl solution in dioxane (2.2 mL, 8.76 mmol) and the reaction mixture is stirred over 18 h at room temperature. The medium is concentrated under reduced pressure, The residue is taken up in 10 mL of water, the pH is adjusted to 8.0 with the addition of a 1 N NaOH aqueous solution followed by 10 mL of water. The solution is lyophilized, the white solid obtained is then solubilized in chloroform (10 mL), concentrated under reduced pressure, toluene (10 mL) is added and the product is concentrated under vacuum once more, this process is repeated twice.

Yield: 0,748 g (97%)

NMR $^1H$ (CDCl$_3$, ppm): 0.87 (6H); 1.05-2.88 (66H); 3.04-3.83 (12H); 4.41-4.83 (3H); 7.74-8.63 (5H)

LC/MS (ESI): 889.8; (calculated ([M+H]$^+$): 889.7)
Copolyamino Acid B1:

In a oven-dried round-bottom flask, γ-benzyl-L-glutamate N-carboxyanhydride (29.3 g, 111 mmol) is solubilized in anhydrous DMF (116 mL). The mixture is stirred under argon until complete solubilization, cooled down to 4° C., then molecule 6 (4.50 g, 5 mmol) in chloroform (15 mL) is rapidly introduced. The mixture is stirred between 4° C. and room temperature over 17 h and heated at 65° C. over 2 h. The reaction mixture is concentrated under reduced pressure until the volume of solvent is half reduced, then poured dropwise in diisopropylether (820 mL) while stirring. After 1 h, the white precipitate is collected by filtration, triturated with diisopropylether until a white powder is obtained then is dried under vacuum at 30° C. to give a white solid. The solid (24.50 g) is dissolved in TFA (95 mL), and a 33% HBr solution in acetic acid (67 mL, 385 mmol) is then added dropwise at 0° C. La solution is stirred over 2.5 h at room temperature then poured dropwise over a 1:1 (v/v) diisopropylether/water mixture while stirring (1.2 L). After stirring for 2 h, the heterogenous mixture is rested overnight. The white precipitate is collected by filtration, then washed twice with diisopropylether (100 mL) and twice with water (100 mL). The solid obtained is solubilized in water (600 mL) by adjustment of the pH to 7.2 using 1 N soda aqueous solution. After solubilization, the theoretical concentration is adjusted to 20 g/L theoritically adding water to obtain a final volume of 900 mL. The mixture is filtered on 0.45 μm frit then purified by ultrafiltration against a 0.9% NaCl solution, a 0.1 N aqueous soda solution, a 0.9% NaCl solution, a phosphate buffer solution, a 0.9% NaCl solution, then water until the conductimetry of the permeate is inferior to 50 μS/cm. The copolyamino acid solution is then concentrated to about 25 g/L theoritically, the pH is adjusted to 7.2 and the solution is filtered on 0.2 μm frit. La solution is then filtered on 0.45 μm frit and purified by ultrafiltration against a 0.9% NaCl solution, then water until the conductimetry of the permeate is inferior to 50 μS/cm. The copolyamino acid solution is then concentrated to about 25 g/L theoritically, filtered on 0.2 μm frit and kept at 2-8° C.

Dry extract: 15.5 mg/g

DP (estimated by NMR $^1H$)=27 that is i=0.037

The calculated number-average molecular weight of copolyamino acid B1 is 4800 g/mol HPLC-SEC aqueous (calibrant PEG): Mn=3650 g/mol

Example B2: Copolyamino Acid B2: Poly-L-Glutamate De Sodium Capped to One of its Extremities with an Acyl Group and Modified with Molecule A2 Having a Number-Average Molecular Weight (Mn) of 3320 g/Mol Copolyamino acid B2-1: poly-L-glutamique acid of relative number-average molecular weight (Mn) relative of 3480 g/mol and DP 22 obtained from the polymerization of γ-benzyl-L-glutamate N-carboxyanhydride initiated using hexylamine and capped to one of its extremities with an acetyl group.

In a 1 L round-bottom flask is added γ-benzyl-L-glutamate N-carboxyanhydride (Glu(OBzl)-NCA, 189 g, 716 mmol), then DMF (425 mL) is introduced. The mixture is then stirred under argon until complete dissolution, cooled down to 4° C., then hexylamine (3.29 g, 32.55 mmol) is rapidly introduced. The mixture is stirred between 4° C. and room temperature over 19 h then poured slowly on diisopropylether (6.3 L) while stirring. After stirring for 3 h, the precipitate is collected by filtration, washed twice with diisopropylether (420 mL) then dried to give a white solid which is solubilized in 850 mL of THF. To this solution are successively added DIPEA (42 g, 325 mmol) and acetic anhydride (33 g, 325 mmol). After stirring overnight at room temperature, la solution is poured slowly over 1 h in diisopropylether (5 L) while stirring. After stirring for 1.5 h, the precipitate is filtered, washed twice with diisopropylether (420 mL) then dried under vacuum to 30° C. to give a poly(gamma-benzyl-L-glutamic) acid capped to one of its extremities with an acetyl group.

To a solution of the copolyamino acid obtained (72 g) in trifluoroacetic acid (TFA, 320 mL) at 4° C., a 33% bromhydric acid solution (HBr) in acetic acid (225 mL, 1.28 mol) is added dropwise over 1 h. The mixture is stirred at room temperature over 2.5 h, then poured dropwise over 1 h on a 1:1 (v/v) diisopropylether and water mixture while stirring (4 L). After stirring for 2 h, the mixture is rested overnight. The precipitate white is collected by filtration, washed with a 1:1 (v/v) diisopropylether and water mixture (320 mL) then with water (320 mL).

The solid obtained is then solubilized in water (1.4 L) by adjusting the pH to 7.5 using a 1 N aqueous soda solution. After solubilisation, the solution is diluted adding water to give a final volume of 2.1 L. The solution is filtered on 0.45 µm frit then purified by ultrafiltration against a 0.9% NaCl solution, then water until the conductimetry of the permeate is inferior to 50 µS/cm. The aqueous solution is then acidified using a 37% chlorhydric acid solution 37% while stirring until a pH of 2 is reached. After stirring for 4 h, the precipitate obtained is filtered, washed with water (320 mL) then dried under vacuum at 30° C. to give a poly-L-glutamic acid of number-average molecular weight (Mn) 3480 g/mol compared to a polyoxyethylene (PEG) standard, and of average polymerization degree 22.

Copolyamino Acid B2:

The copolyamino acid B2-1 of number-average molecular weight (Mn) 3480 g/mol (5.0 g) is solubilized in DMF (60 mL) at 40° C. then kept at this temperature. In parallel, the chlorhydrate salt of molecule A2 (881 mg, 1.11 mmol) is suspended in DMF (5.5 mL) and triethylamine (0.1 g, 1.11 mmol) is added, then the mixture is stirred until complete dissolution. To the copolyamino acid B2-1 in DMF, N-methylmorpholine (NMM, 3.73 g, 37 mmol), the solution of molecule A2 then 2-hydroxypyridine N-oxide (HOPO, 410 mg, 3.69 mmol) are added successively. The reaction medium is then cooled down at 0° C., then N-(3-dimethylaminopropyl)-N'-ethylcarbodiimide (EDC, 707 mg, 3.69 mmol) is added and the medium is risen at room temperature in 4 h. The reaction medium is filtered on 0.2 mm woven frit, poured dropwise on 625 mL of water containing 15% NaCl by weight and HCl (pH 2) under stirring and at 10° C., then the suspension is kept at rest overnight at room temperature. The precipitate is collected by filtration, solubilized in 300 mL of water by slowly adding a 1 N NaOH aqueous solution until pH 7 while stirring, then the solution is filtered on 0.45 µm frit. The clear solution obtained is purified by ultrafiltration against a 0.9% NaCl solution, a carbonate buffer solution, a 0.9% NaCl solution, a phosphate buffer solution, a 0.9% NaCl solution, then water until the conductimetry of the permeate is inferior to 50 µS/cm. The solution is filtered on frit 0.2 µm and kept at 2-8° C.

Dry extract: 18.7 mg/g

DP (estimated according to la NMR $^1$H): 22

According to NMR $^1$H: i=0.032

The calculated number-average molecular weight of B2 is 3974 g/mol.

HPLC-SEC aqueous (calibrant PEG): Mn=3320 g/mol

Example B3: Copolyamino Acid B3-Sodium Poly-L-Glutamate Modified with Molecule A1 Having a Number-Average Molecular Weight (Mn) of 3100 g/Mol Copolyamino acid B3-1: poly-L-glutamic acid of relative number-average molecular weight (Mn) relative of 3390 g/mol and DP 22 obtained from the polymerization of γ-benzyl-L-glutamate N-carboxyanhydride initiated using hexylamine.

In a 1 L round-bottom flask is added γ-benzyl-L-glutamate N-carboxyanhydride (Glu(OBzl)-NCA, 200 g, 760 mmol), then DMF (450 mL) is introduced. The mixture is then stirred until complete dissolution, cooled down at 4° C., then hexylamine (3.94 g, 34.53 mmol) is introduced rapidly. The mixture is stirred between 4° C. and room temperature for 3 days then heated at 80° C. over 2 h. The solution is poured slowly in diisopropylether (6 L) under stirring. After stirring for 1 h, the precipitate is collected by filtration, washed twice with diisopropylether (900 mL) then dried under reduced pressure.

To a solution of copolyamino acid obtained (78 g) in trifluoroacetic acid (TFA, 360 mL) at 4° C., a 33% bromhydric acid solution (HBr) in acetic acid (250 mL, 1.42 mol) is added dropwise over 40 minutes. The mixture is stirred at room temperature over 2.5 h, then poured dropwise on a 1:1 (v/v) diisopropylether and water mixture under stirring (4.2 L). After stirring for 2 h, the mixture is kept at rest overnight. The white precipitate is collected by filtration, washed with a 1:1 (v/v) diisopropylether and water mixture (340 mL) then with water (350 mL).

The solid obtained is then solubilized in water (1.5 L) by adjusting the pH to 7.2 using a 1 N aqueous soda solution. After solubilization, the solution is diluted by addition of water to give a final volume of 2.4 L. The solution is filtered on 0.45 µm frit then purified by ultrafiltration against a 0.9% NaCl solution, then water until the conductimetry of the permeate is inferior to 50 µS/cm. The solution aqueous is then acidified using a 37% chlorhydric acid solution while stirring until a pH of 2 is reached. After 18 h, the precipitate obtained is filtered, washed with water (350 mL) then dried under vacuum to 30° C. to give a poly-L-glutamic acid of number-average molecular weight (Mn) 3390 g/mol compared to a polyoxyethylene (PEG) standard, and of average polymerization degree 22.

Copolyamino Acid B3

Using a similar process than the one used for preparing copolyamino acid B2 and applied to the copolyamino acid B3-1 (5 g) and to molecule A1 (1.11 g, 1.50 mmol), a modified sodium poly-L-glutamate with molecule A1 is obtained.

Dry extract: 22 mg/g

DP (estimated according to la NMR $^1$H): 22

According to NMR $^1$H: i=0.041

The calculated number-average molecular weight of B3 is 3986 g/mol

HPLC-SEC aqueous (calibrant PEG): Mn=3100 g/mol

Example B4: Copolyamino Acid B4-Sodium Poly-L-Glutamate Modified with Molecule A4 Having a Number-Average Molecular Weight (Mn) of 3250 g/Mol In an oven-dried round-bottom flask, γ-benzyl-L-glutamate N-carboxyanhydride (25 g, 95 mmol) is solubilized in anhydrous DMF (50 mL). The mixture is stirred under argon until complete solubilization, cooled down at 4° C., then the molecule A4 (3.22 g, 4.32 mmol) in DMF (10 mL) is introduced rapidly. The mixture is stirred between 4° C. and room temperature for 2 days, heated at 65° C. over 2 h, then cooled down at room temperature and then poured dropwise in diisopropylether (850 mL) under stirring. After 1 h, the precipitate is collected by filtration, triturated with diisopropylether until obtention of a powder then dried under vacuum at 30° C. The solid (22 g) is diluted in TFA (89 mL), and a 33% bromhydric acid solution (HBr) in acetic acid (62 mL, 354 mmol) is then added dropwise and at 0° C. The solution is stirred for 3.5 h at room temperature then poured dropwise on a 1:1 (v/v) diisopropylether/eau mixture and under stirring (1.8 L). After stirring for 2 h, the heterogenous mixture is kept at rest overnight. The white precipitate is collected by filtration, then washed twice with diisopropylether (90 mL) and twice with water (90 mL). The solid obtained is solubilized in water (540 mL) by adjusting the pH to 7.2 using a 1 N aqueous soda solution. After solubilization, the theoretical concentration is adjusted to 20 g/L theoritically by adding water to give a final volume of 810 mL. The mixture is filtered on 0.45 μm frit then is purified by ultrafiltration against a 0.9% NaCl solution then water until the conductimetry of the permeate is inferior to 50 μS/cm. The copolyamino acid solution is then concentrated to about 25 g/L theoritically and filtered on 0.2 μm then kept at 2-8° C.

Dry extract: 23.6 mg/g

DP (estimated according to la NMR $^1$H): 22 that is i=0.045

The calculated number-average molecular weight of B4 is 4030 g/mol

HPLC-SEC aqueous (calibrant PEG): Mn=3250 g/mol

Part C—Compositions Consisting of Insulin Glargine, or Insulin Glargine and Prandial Insulin Example C1: Fast-Acting Insulin Analog Solution (Humalog®) at 100 U/mL This solution is a commercial solution of insulin lispro, marketed by ELI LILLY under the name Humalog®. This product is a fast-acting insulin analog. The excipients in Humalog® are meta-cresol (3.15 mg/mL), glycerol (16 mg/mL), disodium phosphate (1.88 mg/mL), zinc oxide (to have 0.0197 mg of zinc ion/mL), sodium hydroxide and hydrochloric acid to adjust the pH (pH 7-7.8) and water.

Example C2: Solution of Rapid Insulin Analog (NovoLog®) at 100 U/mL

This solution is a commercial solution of insulin aspart marketed by the company NOVO NORDISK under the name of NovoLog® in the United States of America and Novolog® in Europe. This product is a rapid insulin analog. The excipients of Novolog® are glycerol (16 mg), phenol (1.50 mg/mL), meta-cresol (1.72 mg/mL), zinc (19.6 μg/mL), disodium phosphate dihydrate (1.25 mg/mL), sodium chloride (0.5 mg/mL), sodium hydroxide and hydrochloric acid for the adjustment of the pH (pH 7.2-7.6), and water.

Example C3: Solution of Rapid Insulin Analog (Apidra®) at 100 U/mL

This solution is a commercial solution of insulin glulisine marketed by the company SANOFI under the name of Apidra®. This product is a rapid insulin analog. The excipients of Apidra® are meta-cresol (3.15 mg/mL), tromethamine (6 mg/mL), sodium chloride (5 mg/mL), polysorbate 20 (0.01 mg/mL), sodium hydroxide and hydrochloric acid for the adjustment of the pH (pH 7.3), and water.

Example C4: Solution of Slow-Acting Insulin Analog (Lantus®) at 100 U/mL

This solution is a commercial solution of insulin glargine marketed by the company SANOFI under the name of Lantus®. This product is a slow-acting insulin analog. The excipients in Lantus® are zinc chloride (30 μg/mL), meta-cresol (2.7 mg/mL), glycerol (85%) (20 mg/mL), sodium hydroxide and hydrochloric acid for the adjustment of the pH (pH 4) and water.

Example C5: Solution of Human Insulin (ActRapid®) at 100 IU/mL

This solution is a commercial solution of human insulin from NOVO NORDISK sold under the name of ActRapid®. This product is a human insulin. The excipients of ActRapid® are zinc chloride, glycerol, meta-cresol, sodium hydroxide and hydrochloric acid for the adjustment of the pH (pH 6.9-7.8), and water.

Example C6: Solution of Human Insulin (Umuline Rapide®) at 100 IU/mL

This solution is a commercial solution of human insulin from ELI LILLY sold under the name of Umuline Rapide®. This product is a human insulin. The excipients of Umuline Rapide® are glycerol, meta-cresol, sodium hydroxide and hydrochloric acid for the adjustment of the pH (pH 7.0-7.8), and water.

Example C7: Solution of GLP-1 RA Dulaglutide (Trulicity®) at 3 mg/mL

This solution is a solution of dulaglutide marketed by the company ELI LILLY under the name of Trulicity®. The excipients in Trulicity® are anhydrous citric acid (0.14 mg/mL), mannitol (46.4 mg/mL), polysorbate 80 (0.20 mg/mL), trisodium citrate dihydrate (2.74 mg/mL), and water.

Example C8: Solution of GLP-1 RA Exenatide (Byetta®) at 0.25 mg/mL

This solution is a solution of exenatide marketed by the company ELI LILLY under the name of Byetta®. The excipients in Byetta® are meta-cresol (20 mM), mannitol, glacial acetic acid, sodium acetate trihydrate, and water.

a) Compositions Comprising Insulin Glargine

Preparation method CA1: Preparation of a diluted composition of co-polyamino acid/insulin glargine 50 U/mL at pH 7.1, according to a method using insulin glargine in liquid form (in solution) and a co-polyamino acid in liquid form (in solution).

Concentrated solutions of m-cresol and of glycerol are added to a stock solution of co-polyamino acid at pH 7.1 in a manner so as to obtain a solution of co-polyamino acid of concentration $C_{co-polyamino\ acid\ stock/excipients}$ (mg/mL). The quantity of excipients added is adjusted in a manner so as to obtain a concentration of m-cresol of 35 mM and of glycerol of 184 mM in the composition of co-polyamino acid/insulin glargine 50 U/mL at pH 7.1.

In a sterile jar, a volume $V_{insulin\ glargine}$ of a commercial solution of insulin glargine marketed under the name of Lantus® at a concentration of 100 U/mL is added to a volume $V_{co-polyamino\ acid\ stock/excipients}$ of a solution of co-polyamino acid at concentration $C_{co-polyamino\ acid\ stock/excipients}$ (mg/mL) in a manner so as to obtain a diluted composition of co-polyamino acid $C_{diluted\ co-polyamino\ acid}$ (mg/mL)/insulin glargine 50 U/mL at pH 7.1. Turbidity appears. The pH is adjusted to pH 7.1 by addition of concentrated NaOH, and the solution is placed under static conditions in an oven at 40° C. for 2 h until the solubilization is complete. This visually clear solution is placed at +4° C.

Preparation Method CA2: Preparation of a Concentrated Composition of Co-Polyamino Acid/Insulin Glargine at pH 7.1 with the Aid of a Co-Polyamino Acid, According to a Method for Concentrating a Diluted Composition.

A composition of co-polyamino acid/insulin glargine 50 U/mL at pH 7.1 described in Example CA1 is concentrated by ultrafiltration through a 3 kDa membrane made of regenerated cellulose (Amicon® Ultra-15 marketed by the company Millipore). After this ultrafiltration step, the retentate is clear, and the concentration of insulin glargine in the composition is determined by reverse phase chromatography (RP-HPLC). The concentration of insulin glargine in the composition is then adjusted to the desired value by dilution in a solution of excipients m-cresol/glycerol in a manner so as to obtain a final concentration of m-cresol of 35 mM and an osmolarity of 300 mOsm/kg. The pH is measured and adjusted to pH 7.1 by addition of concentrated NaOH and HCl. This solution at pH 7.1, visually clear, has a concentration of insulin glargine $C_{insulin\ glargine}$ (U/mL) and a concentration of co-polyamino acid $C_{co-polyamino\ acid}$ (mg/mL)=$C_{diluted\ co-polyamino\ acid}$ (mg/mL) x $C_{insulin\ glargine}$ (U/mL)/50 (U/mL).

According to this preparation method CA2, compositions of co-polyamino acid/insulin glargine were prepared, for example, with concentrations of insulin glargine of 200 U/mL and 400 U/mL.

Example CA3: Preparation of Compositions of Co-Polyamino Acid/Insulin Glargine 200 U/mL at pH 7.1

Compositions of co-polyamino acid/insulin glargine 200 U/mL are prepared according to the method described in Example CA2 in a manner so as to obtain a concentration of insulin glargine $C_{insulin\ glargine}$=200 U/mL and a concentration of co-polyamino acid $C_{co-polyamino\ acid}$ (mg/mL). These compositions are presented in the following Table 3.

TABLE 3

Composition of insulin glargine (200 U/mL) in presence of copolyamino acid.

| Composition | Copolyamino acid | Concentration in copolyamino acid (in mg/ml) | Insulin glargine (U/mL) |
|---|---|---|---|
| CA3-1 | B1 | 5 | 200 |
| CA3-2 | B2 | 6 | 200 |
| CA3-3 | B3 | 9 | 200 |
| CA3-4 | B4 | 5 | 200 | b) Compositions Comprising Insulin Glargine and Insulin Lispro

Preparation Method CB1: Preparation of a Diluted Composition of Co-Polyamino Acid/Insulin Glargine 43 (U/mL)/Insulin Lispro 13.5 (U/mL)

A volume $V_{insulin\ lispro}$ of a commercial solution of insulin lispro Humalog® at 100 U/mL and water is added to a volume $V_{co-polyamino\ acid/diluted\ insulin\ glargine}$ of the diluted composition of co-polyamino acid/insulin glargine 50 U/mL at pH 7.1 described in Example CA1, in a manner so as to obtain a composition of co-polyamino acid/insulin glargine 43 (U/mL)/insulin lispro 13.5 (U/mL).

Preparation Method CB2: Preparation of a Concentrated Composition of Co-Polyamino Acid/Insulin Glargine/Insulin Lispro at pH 7.1

A composition of co-polyamino acid/insulin glargine 43 (U/mL)/insulin lispro 13.5 (U/mL) described in Example CB1 is concentrated by ultrafiltration through a 3 kDa membrane made of regenerated cellulose (Amicon® Ultra-15 marketed by the company MILLIPORE). After the completion of this ultrafiltration step, the retentate is clear, and the concentration of insulin glargine in the composition is determined by reverse phase chromatography (RP-HPLC). The concentrations of insulin glargine and insulin lispro in the composition are then adjusted to the desired value by dilution in a solution of excipients m-cresol/glycerol in a manner so as to obtain a final concentration of m-cresol of 35 mM and an osmolarity of 300 mOsm/kg. The pH is measured and adjusted if necessary to pH 7.1 by addition of concentrated NaOH and HCl. This solution at pH 7.1, visually clear, has a concentration of insulin glargine $C_{insulin\ glargine}$ (U/mL), a concentration of insulin lispro $C_{insulin\ lispro}$=$C_{insulin\ glargine}$×0.33, and a concentration of co-polyamino acid $C_{co-polyamino\ acid}$ (mg/mL)= $C_{diluted\ co-polyamino\ acid}$ (mg/mL)×$C_{insulin\ glargine}$ (U/mL)/50 (U/mL).

Example CB3: Preparation of Compositions of Co-Polyamino Acid/Insulin Glargine 200 U/mL/Insulin Lispro 66 U/mL at pH 7.1

Des compositions copolyamino acid/insuline glargine 200 U/mL/insuline lispro 66 U/mL are préviaées selon le procédé décrit in l'Example CB2 de manière to obtenir une concentration en insuline glargine $C_{insuline\ glargine}$=200 U/mL, une concentration en insuline lispro $C_{insuline\ lispro}$=66 U/mL and une concentration en copolyamino acid $C_{copolyamino\ acid}$ (mg/mL). Ces compositions are présentées in Compositions of co-polyamino acid/insulin glargine 200 U/mL/insulin lispro 66 U/mL are prepared according to the method described in Example CB2 in a manner so as to obtain a concentration of insulin glargine $C_{insulin\ glargine}$=200 U/mL, a concentration of insulin lispro $C_{insulin\ lispro}$=66 U/mL, and a concentration of co-polyamino acid $C_{co-polyamino\ acid}$ (mg/mL). These compositions are presented in Table 4.

TABLE 4

Composition of insulin glargine (200 U/mL) and of insulin lispro (66 U/mL) in presence of copolyamino acid.

| Composition | Copolyamino acid | Concentration in copolyamino acid (in mg/ml) | Insulin glargine (U/ml) | Insulin Lispro (U/ml) |
|---|---|---|---|---|
| CB3-1 | B1 | 5 | 200 | 66 |
| CB3-2 | B2 | 6 | 200 | 66 |

TABLE 4-continued

Composition of insulin glargine (200 U/mL) and of insulin lispro (66 U/mL) in presence of copolyamino acid.

| Composition | Copolyamino acid | Concentration in copolyamino acid (in mg/ml) | Insulin glargine (U/ml) | Insulin Lispro (U/ml) |
|---|---|---|---|---|
| CB3-3 | B3 | 9 | 200 | 66 |
| CB3-4 | B4 | 5 | 200 | 66 |

Part D—Results

Demonstration of the physical stability of the compositions according to the invention by the study of co-polyamino acid/insulin glargine 200 U/mL compositions and of co-polyamino acid/insulin glargine 200 U/mL/lispro 66 U/mL compositions.

Example D1: Stability Accelerated at 25° C. Under Dynamic Conditions 3 3-mL vials filled with 1 mL of composition co-polyamino acid/insulin glargine are placed vertically in an orbital stirrer. The stirrer is placed in an oven at 25° C., and the vials are subjected to stirring at 250 rpm. The vials are inspected visually daily/weekly in order to detect the appearance of visible particles or turbidity. This inspection is carried out according to the recommendations of the European Pharmacopoeia (EP 2.9.20): the vials are subjected to illumination of at least 2000 lux and are observed on a white background and on a black background. The number of days of stability corresponds to the duration after which at least 2 vials present visible particles or are turbid.

These results are in agreement with the US Pharmacopoeia (USP <790>).

The results of accelerated stability (obtained with different compositions) are presented in Table 5 and Table 6.

TABLE 5 results of the stabilities of the compositions of co-polyamino acid/insulin glargine (200 U/mL)/insulin lispro (66 U/mL) at 25° C. under dynamic conditions (with stirring at 250 rpm).

| Composition | Copolyamino acid | Concentration in copolyamino acid (mg/mL) | Stability (days) |
|---|---|---|---|
| CB3-1 | B1 | 5 | 15 |
| CB3-3 | B3 | 9 | >25 |

TABLE 6 results of the stabilities of the compositions of co-polyamino acid/insulin glargine (200 U/mL) at 25° C. under dynamic conditions (with stirring at 250 rpm).

| Composition | Copolyamino acid | Concentration in copolyamino acid (mg/mL) | Stability (days) |
|---|---|---|---|
| CA3-1 | B1 | 5 | 19 |
| CA3-3 | B3 | 9 | >25 |

Example D2: Solubilization/Precipitation

Example CA4: Precipitation of Insulin Glargine in Compositions of Co-Polyamino Acid/Insulin Glargine at 200 U/mL 1 mL of solution of co-polyamino acid/insulin glargine prepared in Example CA3 is added to 2 mL of a PBS solution containing 20 mg/mL of BSA (bovine serum albumin). The PBS/BSA mixture simulates the composition of the subcutaneous environment. A precipitate appears.

A centrifugation at 4000 rpm is carried out in order to separate the precipitate from the supernatant. Next, the insulin glargine is assayed in the supernatant by RP-HPLC. The result is that insulin glargine is present in majority proportion in a precipitated form.

The results are presented in Table 7:

TABLE 7

Compositions copolyamino acid/insulin glargine (200 U/mL); solubilization/precipitation of insulin glargine.

| Composition | Copolyamino acid | Concentration (mg/ml) | Insulin glargine en (U/mL) | Solubilization of insulin glargine | Precipitation of insulin glargine |
|---|---|---|---|---|---|
| CA3-1 | B1 | 5 | 200 | YES | YES |
| CA3-2 | B2 | 6 | 200 | YES | YES |
| CA3-3 | B3 | 9 | 200 | YES | YES |
| CA3-4 | B4 | 5 | 200 | YES | YES |

Example CB4: Precipitation of Insulin Glargine in the Compositions of Co-Polyamino Acid/Insulin Glargine/Insulin Lispro at 200/66 200/66 U/mL 1 mL of solution of co-polyamino acid/insulin glargine/insulin lispro prepared in Example CB3 is added to 2 mL of a PBS solution containing 20 mg/mL of BSA (bovine serum albumin). The PBS/BSA mixture simulates the composition of the subcutaneous environment. A precipitate appears.

A centrifugation at 4000 rpm is carried out in order to separate the precipitate from the supernatant. Next, the insulin glargine is assayed in the supernatant by RP-HPLC.

The result is that insulin glargine is found in majority proportion in a precipitated form. The results are presented in Table.

TABLE 8

Compositions copolyamino acid/insulin glargine (200 U/mL)/insulin lispro (66 U/mL); solubilization and precipitation of insulin glargine.

| Composition | Copolyamino acid | Concentration in copolyamino acid (mg/ml) | Insulin glargine U/ml | Insulin Lispro U/ml | Solubilization of insulin glargine | Precipitation of insulin glargine |
|---|---|---|---|---|---|---|
| CB3-1 | B1 | 5 | 200 | 66 | YES | YES |
| CB3-2 | B2 | 6 | 200 | 66 | YES | YES |
| CB3-3 | B3 | 9 | 200 | 66 | YES | YES |
| CB3-4 | B4 | 5 | 200 | 66 | YES | YES |

Example D3: Preparation of a Diluted Co-Polyamino Acid/Insulin Glargine 65 U/mL Composition at pH 7.1

Concentrated solutions of m-cresol and of glycerol are added to a stock solution of co-polyamino acid at pH 7 in a manner so as to obtain a solution of co-polyamino acid of concentration $C_{co-polyamino\ acid\ stock/excipients}$ (mg/mL). The quantity of excipients added is adjusted in a manner so as to obtain a concentration of m-cresol of 35 mM and of glycerol of 184 mM in the co-polyamino acid/insulin glargine 65 U/mL composition at pH 7.1.

In a sterile jar, a volume $V_{insulin\ glargine}$ of a commercial solution of insulin glargine marketed under the name of Lantus® at a concentration of 100 U/mL is added to a volume $V_{co-polyamino\ acid\ stock/excipients}$ of a solution of co-polyamino acid of concentration $C_{co-polyamino\ acid\ stock/excipients}$ (mg/mL) in a manner so as to obtain a diluted co-polyamino acid composition $C_{diluted\ co-polyamino\ acid}$ (mg/mL)/insulin glargine 65 U/mL at pH 7.1. Turbidity appears. The pH is adjusted to pH 7.1 by addition of concentrated NaOH, and the solution is placed under static conditions in an oven at 40° C. for 2 h until the solubilization is complete. This visually clear solution is placed at +4° C.

Example D4: Precipitation of a Co-Polyamino Acid/Insulin Glargine 65 U/mL Composition at pH 7.1, by Varying the Concentration of Albumin 0.3 mL of a solution of BSA (bovine serum albumin) in a PBS buffer at pH 7.4 (phosphate buffer saline) and 1 mL of diluted co-polyamino acid/insulin glargine 65 U/mL composition, pH 7.1 are introduced, respectively in a disposable UV cuvette in a manner so as to obtain a mixture containing 50 U/mL insulin glargine, an albumin concentration CBSA (mg/mL) in a PBS buffer. Several solutions of BSA in a PBS buffer of variable concentrations are prepared so as to vary the concentration of albumin in the final mixture from 1 to 12.7 mg/mL (1; 2.9; 3.9; 6.8; 9.7; 12.7 mg/mL) and a concentration of physiological salt via the PBS buffer.

After addition of the solution of BSA in the PBS buffer, the mixture is rapidly homogenized by a few back and forth strokes of a pipette. One hour after the mixing, an absorbance measurement at 500 nm is carried out by means of a JASCO V-530 UV-Vis spectrophotometer.

The absorbance measurement at 500 nm makes it possible to evaluate the turbidity of the mixture originating from the precipitation of the insulin glargine. The turbidity increases as a function of the albumin concentration to reach a plateau reflecting the complete precipitation of the insulin glargine.

The critical albumin concentration allowing a quantitative precipitation is defined as the albumin concentration for which the absorbance value at 500 nm reaches 80% of the absorbance measured at the plateau.

One notes that in the compositions of the invention, the critical BSA quantity is lower.

The results are reported in the following Table.

TABLE 9

Critical albumin concentration (mg/ml) for 80% of precipitation after 1 h (insuline glargine at 50 U/ml).

| Copolyamino acid | Critical albumin concentration (mg/ml) for 80% of precipitation after 1 h (insulin glargine to 50 U/ml) | Concentration of copolyamino acid in solution insuline glargine to 50 U/ml (en mg/ml) |
|---|---|---|
| B1 | <7 | 1.6 |
| B2 | <3 | 1.9 |
| B3 | <1 | 2.9 |
| B4 | <4 | 1.6 |

Example D5: Examples of Pharmacodynamic Studies in Dogs

Studies in dogs were carried out for the purpose of evaluating the pharmacodynamics of insulin after administration of the composition of copolyamino acid B1 and insulins (composition CB3-1).

The hypoglycemic effects of this composition were compared to those of simultaneous but separate injections of insulin glargine (Lantus®) (pH 4) and a prandial insulin lispro (Humalog®) in the proportions of 75% of insulin glargine/25% of insulin lispro (dose/dose).

Ten animals that had fasted for approximately 18 hours received injections in the neck above the interscapular region at the dose of 0.67 U/kg. In the hour preceding the insulin injection 3 blood samples were drawn in order to determine the basal level of glucose. The glycemia is determined over 24 h by means of a glucometer.

The mean pharmacokinetic curves of glucose expressed in deviation percentage of the basal level are represented in FIG. 1.

The pharmacodynamic results obtained with the separate and simultaneous administrations of insulin lispro (Humalog®—example C1) and insulin glargine (Lantus®—example C4) in comparison to those obtained with the composition described in Example CB3-1 are presented in FIG. 1. The hypoglycemic activity of the composition described in Example CB3-1 is biphasic. The first rapid phase is defined by a pronounced decrease of glycemia for approximately 60 minutes, which is characteristic of the rapid effect of insulin lispro. This first phase is also visible with the double Lantus®/Humalog® injection, indicating that the composition according to the invention does not modify the rapid character of Humalog®. After approximately 60 minutes, the glycemia rises up to 3 hours, before a second slower phase characterized by a less pronounced hypoglycemic activity lasting up to 18-20 hours post injection. This basal second phase is characteristic of the basal effect of insulin glargine, also visible with the double injection, indicating that the effect is indeed maintained with the composition according to the invention described in Example CB3-1.

The invention claimed is:

1. A composition in the form of an injectable aqueous solution, whose pH is comprised from 6.0 to 8.0, comprising at least:
   a) a basal insulin whose isoelectric point (pI) is comprised from 5.8 to 8.5;
   b) a co-polyamino acid bearing carboxylate charges and hydrophobic radicals Hy, the co-polyamino acid being constituted of glutamic or aspartic units and the hydrophobic radicals Hy according to the following formula I:

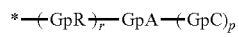

Formula I wherein
GpR is a radical according to formulas II or II':

*—CO—R—CO—*   II or

*—NH—R—CO—*   II';

GpA is a radical according to formula III or III':

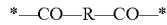   III or

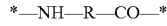   III'

GpC is a radical according to formula IV:

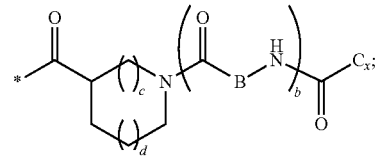   IV the -* indicate the binding sites of the different groups, that is the co-polyamino acids, GpR, GpA and GpC, bound by amide functions;
b is an integer equal to 0 or to 1;
p is an integer equal to 2 or 3 and
   if p is equal to 2 then GpA is a radical according to formula III and,
   if p is equal to 3 then GpA is a radical according to formula III';
c is an integer equal to 0 or 1, and if c is 0 then d is 1 or 2;
d is an integer of 0, 1 or 2;
r is an integer equal to 0 or 1, and
if r is equal to 0, then the hydrophobic radical
according to formula I is bound to the co-polyamino acid through a covalent bond between a carbonyl of the co-polyamino acid and one of the nitrogen atoms of the radical GpA, thereby forming an amide function from the reaction of an amine function, either a primary amine or a secondary amine of the precursor of GpA and an acid function borne by the precursor of the co-polyamino acid, and
if r is equal to 1 or 2, then the hydrophobic radical
according to formula I is bound to the co-polyamino acid:
   through a covalent bond between a nitrogen atom of the radical GpR and a carbonyl of the co-polyamino acid, thus forming an amide function resulting from the reaction of an amine function of the precursor of the radical GpR and an acid function borne by the precursor of the co-polyamino acid or
   through a covalent bond between a carbonyl of the radical GpR and a nitrogen atom in N-terminal position of the co-polyamino acid, thus forming an amide function resulting from the reaction of an acid function of the precursor of the radical GpR and an amine function in N-terminal position borne by the precursor of the co-polyamino acid;
R is a radical chosen from the group consisting of:
a divalent alkyl radical, linear or branched, comprising from 1 to 11 carbon atoms; and
a non-substituted ether or polyether radical
comprising from 4 to 14 carbon atoms and from 1 to 5 oxygen atoms;
A, A' and A" are identical or different and linear or branched alkyl radicals comprising from 2 to 6 carbon atoms;
B is a linear or branched alkyl radical, optionally comprising an aromatic ring, comprising from 1 to 9 carbon atoms;
$C_x$ is a monovalent alkyl radical, linear or branched, in which x indicates the number of carbon atoms and;
if p is equal to 2, x is comprised from 9 to 15 ($9 \leq x \leq 15$);
if p is equal to 3, x is comprised from 7 to 15 ($7 \leq x \leq 15$), the ratio i between the number of hydrophobic radicals and the number of glutamic or aspartic units being from 0 to 0.5 (0<i≤0.5);

when several hydrophobic radicals are carried by a co-polyamino acid they are identical or different;

the degree of polymerization DP of glutamic or aspartic units is comprised from 5 to 250; and the free acid functions being in the form of an alkaline cation salt chosen from the group consisting of $Na^+$ and $K^+$.

2. The composition according to claim 1, wherein Hy comprises from 34 to 70 carbon atoms.

3. The composition according to claim 1, wherein the hydrophobic radicals according to formula I are chosen among the hydrophobic radicals according to formula I wherein p=2, represented in the following formula VI:

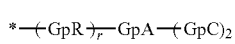

Formula VI wherein GpR, GpA, GpC and r are as defined above.

4. The composition according to claim 3, wherein in the hydrophobic radicals according to formula VI, the radical GpA is chosen from the group consisting of the radicals IIIa and IIIb:

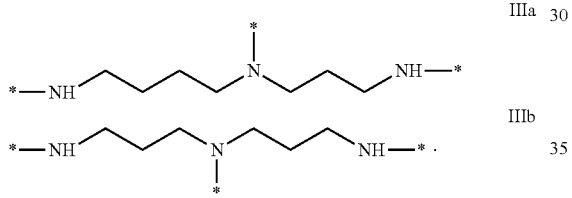

5. The composition according to claim 1, wherein the copolyamino acid bearing carboxylate charges and hydrophobic radicals is chosen among the copolyamino acids according to the following formula VII:

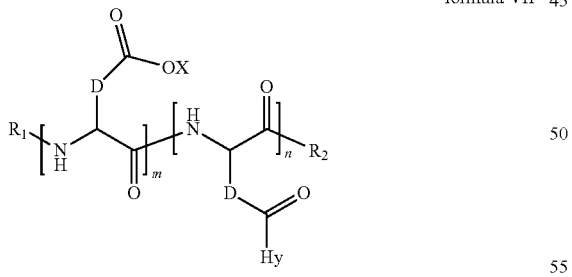

formula VII wherein,

D is, independently, either a —CH2- group (aspartic unit) or a —CH2-CH2- group (glutamic unit), Hy is a hydrophobic radical chosen among the hydrophobic radicals according to formula I:

Formula I formula VI:

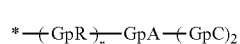

Formula VI wherein GpR, GpA, GpC and r are as defined above, or formula IX:

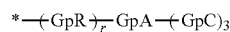

Formula IX wherein GpA is according to formula III' and GpR, GpC and r are as defined above, $R_1$ is a hydrophobic radical chosen among the hydrophobic radicals according to formula I, VI or IX wherein r=0 or r=1 and GpR is a radical according to formula II, or $R_1$ is a radical chosen in the group constituted by a H, a C2 to C10 linear acylated group, a C3 to C10 branched acylated group, a benzyl, a terminal amino acid unit and a pyroglutamate, $R_2$ is a hydrophobic radical chosen among the hydrophobic radicals according to formula I, VI or IX wherein r=0 or r=1 and GpR is a radical according to formula II', or $R_2$ is a —NR'R", R' and R" identical or different being chosen in the group consisting of H, C2 to C10 linear, branched or cyclic alkyls, benzyl and said R' and R" alkyls may form together one or several saturated, unsaturated and/or aromatic carbon rings and/or may include heteroatoms, chosen in the group consisting of O, N and S;

X is a cationic entity chosen in the group consisting of the alkali metal cations; n+m refers to the degree of polymerization DP of the co-polyamino acid, that is the mean number of monomeric unit in a co-polyamino acid chain and 5≤n+m≤250.

6. The composition according to claim 5, wherein the co-polyamino acid bearing carboxylate charges and hydrophobic radicals is chosen among the co-polyamino acids according to formula VII, wherein $R_1=R'_1$ and $R_2=R'_2$, according to the following formula VIIa:

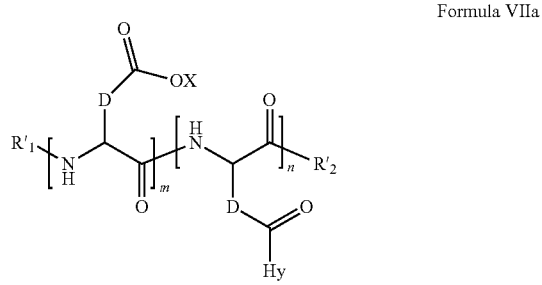

Formula VIIa wherein, m, n, X, D and Hy are as defined above, $R'_1$ is a radical chosen in the group constituted by H, a C2 to C10 linear acylated group, a C3 to C10 branched acylated group, a benzyl, a terminal amino acid unit and a pyroglutamate, $R'_2$ is a radical —NR'R", R' and R" identical or different being chosen in the group consisting of H, C2 to C10 linear, branched or cyclic alkyl and benzyl and said R' and R" alkyls may form together one or several saturated, unsaturated and/or aromatic carbon rings and/or may include heteroatoms, chosen in the group consisting of O, N and S.

7. The composition according to claim 5, wherein the co-polyamino acid bearing carboxylate charges and hydrophobic radicals is chosen among the co-polyamino acids according to formula VII wherein n=0 according to formula VIIb:

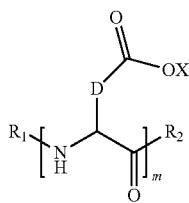

Formula VIIb wherein m, X, D, $R_1$ and $R_2$ are as defined above and at least one of $R_1$ or $R_2$ is a hydrophobic radical according to formula I, VI or IX.

8. The composition according to claim 7, wherein the co-polyamino acid bearing carboxylate charges and hydrophobic radicals is chosen among the co-polyamino acids according to formula VIIb wherein $R_1$ is a hydrophobic radical according to formula I, VI or IX wherein r=1 and GpR is according to formula II.

9. The composition according to claim 7, wherein the co-polyamino acid bearing carboxylate charges and hydrophobic radicals is chosen among the co-polyamino acids according to formula VIIb wherein $R_2$ is a hydrophobic radical according to formula I, VI or IX wherein r=0 or r=1 and GpR is according to formula II'.

10. The composition according to claim 1, wherein the basal insulin for which the isoelectric point is comprised from 5.8 to 8.5 is insulin glargine.

11. The composition according to claim 1, wherein the basal insulin for which the isoelectric point is comprised from 5.8 to 8.5 is a bio-similar insulin glargine.

12. The composition according to claim 1, wherein the composition comprises from 40 to 500 U/mL of basal insulin for which the isoelectric point is comprised from 5.8 to 8.5.

13. The composition according to claim 1, wherein the mass ratio between the basal insulin, for which the isoelectric point is comprised from 5.8 to 8.5, and the co-polyamino acid, that is co-polyamino acid/basal insulin, is comprised from 0.2 to 8.

14. The composition according to claim 1, wherein the composition further comprises a prandial insulin.

15. The composition according to claim 14, wherein the prandial insulin is a recombinant human insulin.

16. The composition according to claim 14, wherein the prandial insulin is chosen in the group consisting of insulin lispro, insulin glulisine and insulin aspart.

17. The composition according to claim 1, wherein the composition further comprises a gastrointestinal hormone.

18. The composition according to claim 17, wherein the gastrointestinal hormone is one of GLP-1 RA analogues or derivatives chosen in the group consisting of exenatide, liraglutide, lixisenatide, albiglutide or dulaglutide, their analogues or derivatives and their pharmaceutically acceptable salts.

* * * * *